(12) United States Patent
Deransart et al.

(10) Patent No.: US 11,779,471 B2
(45) Date of Patent: Oct. 10, 2023

(54) APPARATUSES AND METHODS FOR IMPLANTING GLENOID PROSTHESES

(71) Applicant: HOWMEDICA OSTEONICS CORP., Mahwah, NJ (US)

(72) Inventors: Pierric Deransart, Saint Martin d'uriage (FR); William J. Slone, Silver Lake, IN (US); Robert J. Ball, West Olive, MI (US); Gilles Walch, Lyons (FR); Pascal Boileau, Nice (FR); George S. Athwal, London (CA); Jon J. P. Warner, Weston, IA (US); Robert Z. Tashjian, Salt Lake City, UT (US); Jay D. Keener, St. Louis, MO (US); Charles L. Penninger, Warsaw, IN (US); Ryan D. Koepke, Fort Wayne, IN (US); Matthew Victor Kartholl, Fort Wayne, IN (US); Marine Godelu, Grenoble (FR); Douglas Charles Garman, Fort Wayne, IN (US)

(73) Assignee: HOWMEDICA OSTEONICS CORP., Mahwah, NJ (US)

( * ) Notice: Subject to any disclaimer, the term of this patent is extended or adjusted under 35 U.S.C. 154(b) by 19 days.

(21) Appl. No.: 17/172,789

(22) Filed: Feb. 10, 2021

(65) Prior Publication Data
US 2021/0220151 A1 Jul. 22, 2021

Related U.S. Application Data

(63) Continuation-in-part of application No. PCT/US2020/045211, filed on Aug. 6, 2020.
(Continued)

(51) Int. Cl.
*A61F 2/30* (2006.01)
*A61F 2/40* (2006.01)
(Continued)

(52) U.S. Cl.
CPC ........ *A61F 2/4612* (2013.01); *A61B 17/1684* (2013.01); *A61B 17/1778* (2016.11);
(Continued)

(58) Field of Classification Search
None
See application file for complete search history.

(56) References Cited

U.S. PATENT DOCUMENTS

| 4,725,280 A | 2/1988 | Laure |
| 4,986,833 A | 1/1991 | Worland |

(Continued)

FOREIGN PATENT DOCUMENTS

| DE | 10123517 C1 | 11/2002 |
| EP | 0581667 | 2/1994 |

(Continued)

OTHER PUBLICATIONS

International Search Report and Written Opinion issued in connection with International Patent Application No. PCT/US2022/035217, dated Nov. 1, 2022, 14 pages.

(Continued)

*Primary Examiner* — Ann Schillinger
(74) *Attorney, Agent, or Firm* — Duane Morris LLP

(57) ABSTRACT

Various apparatus and methods for implanting glenoid prostheses are disclosed. In various embodiments, a method for performing shoulder surgery can include guiding a guide pin into the glenoid surface along a reaming axis. A partial reaming guide can be placed in contact with the glenoid surface over the guide pin. A reamer can be guided over the guide pin to ream the glenoid surface. The reamer can be further advanced over the guide pin until the reamer contacts the partial reaming guide, whereby such contact limits reaming to only a portion of the glenoid surface.

15 Claims, 20 Drawing Sheets

Related U.S. Application Data

(60) Provisional application No. 62/885,033, filed on Aug. 9, 2019.

(51) Int. Cl.
*A61B 17/00* (2006.01)
*A61B 17/17* (2006.01)
*A61B 17/88* (2006.01)
*A61B 34/10* (2016.01)
*A61B 17/15* (2006.01)
*A61F 2/46* (2006.01)
*A61B 17/16* (2006.01)
*A61B 17/56* (2006.01)

(52) U.S. Cl.
CPC ........ *A61F 2/30749* (2013.01); *A61F 2/4081* (2013.01); *A61B 2017/564* (2013.01); *A61F 2002/4633* (2013.01)

(56) References Cited

U.S. PATENT DOCUMENTS

| | | |
|---|---|---|
| 5,032,132 A | 7/1991 | Matsen, III et al. |
| 5,033,036 A | 7/1991 | Ohmori et al. |
| 5,080,673 A | 1/1992 | Burkhead et al. |
| 5,108,446 A | 4/1992 | Wagner et al. |
| 5,458,637 A | 10/1995 | Hayes |
| 5,489,309 A | 2/1996 | Lackey et al. |
| 5,489,311 A | 2/1996 | Cipolletti |
| 5,531,973 A | 7/1996 | Sarv |
| 5,662,657 A | 9/1997 | Carn |
| 5,702,447 A | 12/1997 | Walch et al. |
| 5,800,551 A | 9/1998 | Williamson et al. |
| 5,954,722 A | 9/1999 | Bono |
| 6,102,951 A | 8/2000 | Sutter et al. |
| 6,102,954 A | 8/2000 | Albrektsson et al. |
| 6,139,550 A | 10/2000 | Michelson |
| 6,171,342 B1 | 1/2001 | O'Neil et al. |
| 6,228,119 B1 | 5/2001 | Ondrla et al. |
| 6,228,120 B1 | 5/2001 | Leonard et al. |
| 6,406,495 B1 | 6/2002 | Schoch |
| 6,508,841 B2 | 1/2003 | Martin et al. |
| 6,514,287 B2 | 2/2003 | Ondrla et al. |
| 6,673,115 B2 | 1/2004 | Resch et al. |
| 6,679,916 B1 | 1/2004 | Frankle et al. |
| 6,699,289 B2 | 3/2004 | Iannotti et al. |
| 6,761,740 B2 | 7/2004 | Tornier |
| 6,783,549 B1 | 8/2004 | Stone et al. |
| 6,790,234 B1 | 9/2004 | Frankle |
| 6,860,903 B2 | 3/2005 | Mears et al. |
| 6,911,047 B2 | 6/2005 | Rockwood, Jr. et al. |
| 6,942,699 B2 | 9/2005 | Stone et al. |
| 6,953,478 B2 | 10/2005 | Bouttens et al. |
| 6,969,406 B2 | 11/2005 | Tornier |
| 7,160,328 B2 | 1/2007 | Rockwood, Jr. et al. |
| 7,169,184 B2 | 1/2007 | Pria |
| 7,175,663 B1 | 2/2007 | Stone |
| 7,175,665 B2 | 2/2007 | German et al. |
| 7,204,854 B2 | 4/2007 | Guederian et al. |
| 7,316,715 B2 | 1/2008 | Plaskon |
| 7,431,736 B2 | 10/2008 | Maroney et al. |
| 7,462,197 B2 | 12/2008 | Tornier |
| 7,462,199 B2 | 12/2008 | Justin et al. |
| 7,527,631 B2 | 5/2009 | Maroney et al. |
| 7,604,665 B2 | 10/2009 | Iannotti et al. |
| 7,608,109 B2 | 10/2009 | Dalla Pria |
| 7,611,539 B2 | 11/2009 | Bouttens et al. |
| 7,621,961 B2 | 11/2009 | Stone |
| 7,637,928 B2 | 12/2009 | Fernandez |
| 7,648,530 B2 | 1/2010 | Habermeyer et al. |
| 7,666,522 B2 | 2/2010 | Justin et al. |
| 7,753,959 B2 | 7/2010 | Berelsman et al. |
| 7,766,969 B2 | 8/2010 | Justin et al. |
| 7,854,768 B2 | 12/2010 | Wiley et al. |
| 7,883,653 B2 | 2/2011 | Smith et al. |
| 7,892,287 B2 | 2/2011 | Deffenbaugh |
| 7,922,769 B2 | 4/2011 | Deffenbaugh et al. |
| 7,927,335 B2 | 4/2011 | Deffenbaugh et al. |
| 7,993,408 B2 | 8/2011 | Meridew et al. |
| 8,007,523 B2 | 8/2011 | Wagner et al. |
| 8,048,161 B2 | 11/2011 | Guederian et al. |
| 8,062,376 B2 | 11/2011 | Shultz et al. |
| 8,070,820 B2 | 12/2011 | Winslow et al. |
| 8,092,545 B2 | 1/2012 | Coon et al. |
| 8,206,453 B2 | 6/2012 | Cooney, III et al. |
| 8,231,683 B2 | 7/2012 | Lappin et al. |
| 8,241,365 B2 | 8/2012 | Williams, Jr. et al. |
| 8,287,600 B2 | 10/2012 | Angibaud |
| 8,308,807 B2 | 11/2012 | Seebeck et al. |
| 8,357,201 B2 | 1/2013 | Mayer et al. |
| 8,361,157 B2 | 1/2013 | Bouttens et al. |
| 8,425,614 B2 | 4/2013 | Winslow et al. |
| 8,444,680 B2 | 5/2013 | Dooney, Jr. et al. |
| 8,449,617 B1 | 5/2013 | McDaniel et al. |
| 8,454,702 B2 | 6/2013 | Smits et al. |
| 8,454,705 B2 | 6/2013 | Pressacco et al. |
| 8,465,548 B2 | 6/2013 | Long |
| 8,480,750 B2 | 7/2013 | Long |
| 8,532,806 B1 | 9/2013 | Masson |
| 8,556,901 B2 * | 10/2013 | Anthony ............ A61B 17/1659 606/177 |
| 8,556,902 B2 | 10/2013 | Ek et al. |
| 8,556,980 B2 | 10/2013 | Deffenbaugh |
| 8,556,981 B2 | 10/2013 | Jones et al. |
| 8,591,591 B2 | 11/2013 | Winslow et al. |
| 8,597,334 B2 | 12/2013 | Mocanu |
| 8,632,597 B2 | 1/2014 | Lappin |
| 8,690,951 B2 | 4/2014 | Baum et al. |
| 8,690,952 B2 | 4/2014 | Dallmann |
| 8,753,402 B2 | 6/2014 | Winslow et al. |
| 8,790,402 B2 | 7/2014 | Monaghan et al. |
| 8,840,676 B2 | 9/2014 | Belew |
| 8,864,834 B2 | 10/2014 | Boileau et al. |
| 8,870,886 B2 | 10/2014 | Burgi |
| 8,961,611 B2 | 2/2015 | Long |
| 9,114,017 B2 | 8/2015 | Lappin |
| 9,233,003 B2 | 6/2016 | Roche et al. |
| 9,498,345 B2 | 11/2016 | Burkhead et al. |
| 9,512,445 B2 | 12/2016 | Iannotti |
| 9,629,725 B2 | 4/2017 | Gargac et al. |
| 9,763,682 B2 * | 9/2017 | Bettenga ............ A61B 17/1666 |
| 9,839,436 B2 * | 12/2017 | Kehres ............... A61B 17/1684 |
| 10,034,757 B2 | 7/2018 | Kovacs et al. |
| 10,064,734 B2 | 9/2018 | Burkhead et al. |
| 10,251,755 B2 | 4/2019 | Boileau et al. |
| 10,342,669 B2 | 7/2019 | Hopkins |
| 10,357,373 B2 | 7/2019 | Gargac et al. |
| 10,463,499 B2 | 11/2019 | Emerick et al. |
| 10,583,012 B1 | 3/2020 | Longobardi |
| 10,722,374 B2 | 7/2020 | Hodorek et al. |
| 10,779,952 B2 | 9/2020 | Gunther et al. |
| 10,918,492 B2 | 2/2021 | Burkhead et al. |
| 10,945,862 B2 * | 3/2021 | Roby .................... A61F 2/4081 |
| 2001/0011192 A1 | 8/2001 | Ondrla et al. |
| 2001/0037153 A1 | 11/2001 | Rockwood et al. |
| 2002/0095214 A1 | 7/2002 | Hyde, Jr. |
| 2003/0055507 A1 | 3/2003 | McDevitt et al. |
| 2003/0149485 A1 | 8/2003 | Tornier |
| 2004/0030394 A1 | 2/2004 | Horber |
| 2004/0059424 A1 | 3/2004 | Guederian et al. |
| 2004/0106928 A1 | 6/2004 | Ek |
| 2004/0220673 A1 | 11/2004 | Pria |
| 2004/0220674 A1 | 11/2004 | Pria |
| 2005/0049709 A1 | 3/2005 | Tornier |
| 2005/0060039 A1 | 3/2005 | Cyprien |
| 2005/0143831 A1 | 6/2005 | Justin et al. |
| 2005/0149044 A1 | 7/2005 | Justin et al. |
| 2005/0192673 A1 | 9/2005 | Saltzman et al. |
| 2005/0261775 A1 | 11/2005 | Baum et al. |
| 2005/0278030 A1 | 12/2005 | Tornier |
| 2006/0069443 A1 | 3/2006 | Deffenbaugh et al. |
| 2006/0069444 A1 | 3/2006 | Deffenbaugh |
| 2006/0074353 A1 | 4/2006 | Deffenbaugh et al. |

(56) References Cited

U.S. PATENT DOCUMENTS

| | | |
|---|---|---|
| 2006/0074430 A1* | 4/2006 | Deffenbaugh ..... A61B 17/1778 606/87 |
| 2006/0100714 A1 | 5/2006 | Ensign |
| 2006/0111787 A1 | 5/2006 | Bailie et al. |
| 2006/0122705 A1 | 6/2006 | Morgan |
| 2006/0142865 A1 | 6/2006 | Hyde, Jr. |
| 2006/0200248 A1 | 9/2006 | Beguin et al. |
| 2006/0200249 A1 | 9/2006 | Beguin et al. |
| 2007/0016304 A1 | 1/2007 | Chudik |
| 2007/0055380 A1 | 3/2007 | Berelsman et al. |
| 2007/0100458 A1 | 5/2007 | Dalla Pria |
| 2007/0142921 A1 | 6/2007 | Lewis et al. |
| 2007/0156246 A1 | 7/2007 | Meswania et al. |
| 2007/0179624 A1 | 8/2007 | Stone et al. |
| 2007/0219638 A1 | 9/2007 | Jones et al. |
| 2007/0244563 A1 | 10/2007 | Roche et al. |
| 2007/0244564 A1 | 10/2007 | Ferrand et al. |
| 2008/0140130 A1 | 6/2008 | Chan et al. |
| 2008/0183297 A1 | 7/2008 | Boileau et al. |
| 2008/0269906 A1 | 10/2008 | Iannotti et al. |
| 2008/0294268 A1 | 11/2008 | Baum et al. |
| 2008/0306601 A1 | 12/2008 | Dreyfuss |
| 2009/0125113 A1 | 5/2009 | Guederian et al. |
| 2009/0149961 A1 | 6/2009 | Dallmann |
| 2009/0164021 A1 | 6/2009 | Dallmann |
| 2009/0204225 A1 | 8/2009 | Meridew et al. |
| 2009/0216332 A1 | 8/2009 | Splieth et al. |
| 2009/0281630 A1 | 11/2009 | Delince et al. |
| 2009/0292364 A1 | 11/2009 | Linares |
| 2010/0016975 A1 | 1/2010 | Iannotti et al. |
| 2010/0023068 A1 | 1/2010 | Bouttens et al. |
| 2010/0049327 A1 | 2/2010 | Isch et al. |
| 2010/0087927 A1 | 4/2010 | Roche et al. |
| 2010/0161066 A1 | 6/2010 | Iannotti et al. |
| 2010/0217399 A1 | 8/2010 | Groh |
| 2010/0234959 A1 | 9/2010 | Roche et al. |
| 2010/0249938 A1 | 9/2010 | Gunther et al. |
| 2010/0274359 A1 | 10/2010 | Brunnarius et al. |
| 2010/0291401 A1 | 11/2010 | Medina et al. |
| 2010/0331990 A1 | 12/2010 | Mroczkowski |
| 2011/0035013 A1 | 2/2011 | Winslow et al. |
| 2011/0106266 A1 | 5/2011 | Schwyzer et al. |
| 2011/0118846 A1 | 5/2011 | Katrana et al. |
| 2011/0144758 A1 | 6/2011 | Deffenbaugh |
| 2011/0144760 A1 | 6/2011 | Wong et al. |
| 2011/0152869 A1* | 6/2011 | Ek ........................... A61F 2/461 606/80 |
| 2011/0190899 A1 | 8/2011 | Pierce et al. |
| 2011/0282393 A1 | 11/2011 | Garlach et al. |
| 2012/0004733 A1 | 1/2012 | Hodorek et al. |
| 2012/0029647 A1 | 2/2012 | Winslow et al. |
| 2012/0059383 A1 | 3/2012 | Murphy et al. |
| 2012/0109320 A1 | 5/2012 | Walch et al. |
| 2012/0123419 A1 | 5/2012 | Purdy et al. |
| 2012/0130498 A1 | 5/2012 | Long |
| 2012/0165954 A1 | 6/2012 | Nimal |
| 2012/0191201 A1 | 7/2012 | Smits et al. |
| 2012/0209392 A1 | 8/2012 | Angibaud et al. |
| 2012/0221111 A1 | 8/2012 | Burkhead et al. |
| 2012/0221112 A1 | 8/2012 | Lappin |
| 2012/0232670 A1 | 9/2012 | Bojarski et al. |
| 2012/0239051 A1 | 9/2012 | de Wilde et al. |
| 2012/0239156 A1 | 9/2012 | De Wilde et al. |
| 2012/0253467 A1 | 10/2012 | Frankle |
| 2012/0277880 A1 | 11/2012 | Winslow et al. |
| 2013/0018483 A1 | 1/2013 | Li et al. |
| 2013/0053968 A1 | 2/2013 | Nardini et al. |
| 2013/0066433 A1 | 3/2013 | Veronesi et al. |
| 2013/0096631 A1 | 4/2013 | Leung et al. |
| 2013/0110116 A1* | 5/2013 | Kehres ............... A61B 17/1739 606/96 |
| 2013/0110470 A1 | 5/2013 | Vanasse et al. |
| 2013/0144393 A1 | 6/2013 | Mutchler et al. |
| 2013/0150972 A1 | 6/2013 | Iannotti et al. |
| 2013/0150973 A1 | 6/2013 | Splieth et al. |
| 2013/0150975 A1 | 6/2013 | Iannotti et al. |
| 2013/0226309 A1 | 8/2013 | Daigo et al. |
| 2013/0231754 A1 | 9/2013 | Daigo et al. |
| 2013/0253656 A1 | 9/2013 | Long |
| 2013/0261751 A1 | 10/2013 | Lappin |
| 2013/0261752 A1 | 10/2013 | Lappin et al. |
| 2013/0264749 A1 | 10/2013 | Jones et al. |
| 2013/0282135 A1 | 10/2013 | Sun et al. |
| 2014/0025173 A1 | 1/2014 | Cardon et al. |
| 2014/0142711 A1 | 5/2014 | Maroney et al. |
| 2014/0194995 A1 | 7/2014 | Koka |
| 2014/0257499 A1 | 9/2014 | Winslow et al. |
| 2014/0277180 A1 | 9/2014 | Paolino et al. |
| 2014/0277518 A1 | 9/2014 | Iannotti |
| 2014/0277520 A1 | 9/2014 | Chavarria et al. |
| 2014/0371863 A1 | 12/2014 | Vanasse et al. |
| 2015/0073424 A1* | 3/2015 | Couture ............. A61B 17/1778 606/96 |
| 2015/0094819 A1 | 4/2015 | Iannotti et al. |
| 2015/0142122 A1 | 5/2015 | Bickley et al. |
| 2015/0150688 A1 | 6/2015 | Vanasse et al. |
| 2015/0265292 A1* | 9/2015 | Olson ................ A61B 17/1684 606/80 |
| 2015/0272741 A1 | 10/2015 | Taylor et al. |
| 2015/0305877 A1 | 10/2015 | Gargac et al. |
| 2016/0045323 A1 | 2/2016 | Kovacs et al. |
| 2016/0166392 A1 | 6/2016 | Vanasse et al. |
| 2016/0199074 A1 | 7/2016 | Winslow et al. |
| 2016/0228262 A1 | 8/2016 | Bailey |
| 2016/0256222 A1* | 9/2016 | Walch .................... A61B 34/10 |
| 2016/0270922 A1 | 9/2016 | Pressacco et al. |
| 2016/0287401 A1 | 10/2016 | Muir et al. |
| 2016/0310285 A1* | 10/2016 | Kovacs .............. A61B 17/1778 |
| 2016/0324649 A1 | 11/2016 | Hodorek et al. |
| 2017/0027709 A1 | 2/2017 | Winslow et al. |
| 2017/0042687 A1 | 2/2017 | Boileau et al. |
| 2017/0042690 A1 | 2/2017 | Burkhead et al. |
| 2017/0049574 A1 | 2/2017 | Hopkins |
| 2017/0172764 A1 | 6/2017 | Muir et al. |
| 2017/0273795 A1 | 9/2017 | Neichel et al. |
| 2017/0273801 A1 | 9/2017 | Hodorek et al. |
| 2017/0273806 A1 | 9/2017 | Cardon et al. |
| 2018/0014941 A1 | 1/2018 | Frankle et al. |
| 2018/0064537 A1 | 3/2018 | Pressacco et al. |
| 2018/0078377 A1 | 3/2018 | Gargac et al. |
| 2018/0085226 A1 | 3/2018 | Baumgarten |
| 2018/0092747 A1 | 4/2018 | Hopkins |
| 2018/0161169 A1 | 6/2018 | Cardon et al. |
| 2018/0243102 A1 | 8/2018 | Burkhead, Jr. et al. |
| 2018/0368982 A1 | 12/2018 | Ball |
| 2019/0015116 A1 | 1/2019 | Gargac et al. |
| 2019/0015221 A1* | 1/2019 | Neichel ................ A61F 2/4081 |
| 2019/0029833 A1 | 1/2019 | Briscoe et al. |
| 2019/0076261 A1 | 3/2019 | Mutchler et al. |
| 2019/0336293 A1 | 11/2019 | Kehres |
| 2020/0030108 A1 | 1/2020 | Orphanos et al. |
| 2020/0179126 A1 | 6/2020 | Courtney, Jr. et al. |
| 2020/0188121 A1 | 6/2020 | Boux De Casson et al. |
| 2020/0188125 A1 | 6/2020 | Hodorek et al. |
| 2020/0237519 A1 | 7/2020 | Ball et al. |
| 2020/0289180 A1 | 9/2020 | Martin et al. |
| 2020/0289282 A1 | 9/2020 | Lefebvre et al. |
| 2020/0368031 A1 | 11/2020 | Hodorek et al. |
| 2020/0405491 A1 | 12/2020 | Cleveland et al. |
| 2021/0030552 A1 | 2/2021 | Terrill |
| 2021/0030553 A1 | 2/2021 | Terrill |
| 2021/0307911 A1 | 10/2021 | Metcalfe et al. |
| 2021/0338456 A1* | 11/2021 | Wolfe ................... A61F 2/4612 |
| 2021/0369465 A1 | 12/2021 | Simoes et al. |
| 2022/0151794 A1 | 5/2022 | Fattori et al. |
| 2022/0175543 A1 | 6/2022 | Ball |
| 2022/0202580 A1 | 6/2022 | Wilkins et al. |
| 2022/0241077 A1 | 8/2022 | Hodorek et al. |
| 2022/0280306 A1 | 9/2022 | Metcalfe et al. |
| 2022/0296381 A1 | 9/2022 | Ek et al. |
| 2022/0313440 A1 | 10/2022 | Metcalfe et al. |
| 2022/0395376 A1 | 12/2022 | Poon et al. |

(56) References Cited

U.S. PATENT DOCUMENTS

| | | |
|---|---|---|
| 2023/0000636 A1 | 1/2023 | Dalla Pria et al. |
| 2023/0114073 A1 | 4/2023 | Perego |

FOREIGN PATENT DOCUMENTS

| | | | |
|---|---|---|---|
| EP | 0776636 | | 6/1997 |
| EP | 1013246 | | 11/1999 |
| EP | 1064890 | | 1/2001 |
| EP | 1323395 | | 7/2003 |
| EP | 1488764 | B1 | 12/2006 |
| EP | 1762201 | A1 | 3/2007 |
| EP | 1515758 | B1 | 3/2009 |
| EP | 2057970 | | 5/2009 |
| EP | 1639966 | B1 | 9/2009 |
| EP | 1927328 | B1 | 1/2011 |
| EP | 1902689 | B1 | 11/2011 |
| EP | 1996125 | B1 | 5/2013 |
| EP | 2335655 | B1 | 7/2013 |
| EP | 1951161 | B1 | 4/2014 |
| EP | 1973498 | B1 | 4/2014 |
| EP | 2481376 | B1 | 4/2014 |
| EP | 2601912 | B1 | 7/2016 |
| EP | 3291768 | B1 | 11/2019 |
| EP | 3679900 | A1 * | 7/2020 ............. A61B 17/15 |
| FR | 2567019 | | 1/1986 |
| FR | 2567019 | W | 1/1986 |
| FR | 2739151 | A1 | 3/1997 |
| FR | 2776506 | B1 | 8/2000 |
| FR | 2825263 | A1 | 12/2002 |
| FR | 2821545 | B1 | 8/2003 |
| FR | 2955248 | B1 | 3/2012 |
| FR | 2971144 | A1 | 8/2012 |
| FR | 2977791 | B1 | 7/2014 |
| GB | 2297257 | A | 7/1996 |
| WO | WO 2011/073169 | | 6/2011 |
| WO | WO 2011/150180 | A2 | 12/2011 |
| WO | WO 2015/068035 | | 5/2015 |
| WO | WO 2015/103090 | | 7/2015 |
| WO | WO 2017/007565 | | 1/2017 |
| WO | WO 2019/079104 | | 4/2019 |
| WO | 2020154611 | A1 | 7/2020 |
| WO | 2020219962 | A1 | 10/2020 |
| WO | WO 2020/231657 | | 11/2020 |
| WO | 2021178418 | A1 | 9/2021 |

OTHER PUBLICATIONS

Non-Final Office Action issued in connection with U.S. Appl. No. 16/756,429, dated May 6, 2022, 24 pages.
International Search Report and Written Opinion issued in connection with International Patent Application No. PCT/US2022/011217, dated May 4, 2022, 15 pages.
International Search Report and Written Opinion issued in connection with International Patent Application No. PCT/US2022/06106, dated May 11, 2022, 12 pages.
International Search Report and Written Opinion issued in connection with International Patent Application No. PCT/US2022/034245, dated Sep. 23, 2022, 16 pages.
EP Search Report and Written Opinion issued in European Patent Application No. 12153346.7, dated Mar. 8, 2012, in 6 pages.
French Search Report and Written Opinion issued in Application. No. FR1150994, ddated May 27, 2011, in 7 pages.
Anatomical Shoulder™ Inverse/Reverse System Surgical Technique, Product Brochure, Zimmer, Inc., published 2006, in 32 pages.
Arthrex, "Arthrex Releases Univers Revers™ Shoulder Arthroplasty System in the United States—First Surgery Successfully Performed in Chillicothe, OH", Jun. 18, 2013.
Biomet, "Comprehensive® Reverse Shoulder System", 2013.
Boileau et al., "Cemented polyethylene versus uncemented metal-backed glenoid components in total shoulder arthroplasty: A prospective, double-blind, randomized study," Journal of Shoulder and Elbow Surgery, Jul./Aug. 2002, vol. 11, Issue 4, pp. 351-359.
Boileau et al., "Metal-backed glenoid implant with polyethylene insert is not a viable long-term therapeutic option," Journal of Shoulder and Elbow Surgery, Feb. 2015, pp. 1-10.
Cementless Fixation Using a Polyethyene Oseo-Integration Peg as Used on the Freeman-Samuelson Knee brochure, produced by Finsbury Instruments Limited London in conjunction with Adrian Tuke Limited, 1982.
Castagna et al., "Mid-term results of a metal-backed glenoid component in total shoulder replacement," The Journal of Bone and Joint Surgery, Oct. 2010, vol. 92-B, No. 10, pp. 1410-1415.
Clement et al., "An uncemented metal-backed glenoid component in total shoulder arthroplasty for osteoarthritis: factors affecting survival and outcome," The Japanese Orthopaedic Association, published online Sep. 26, 2012, vol. 18, pp. 22-28.
Djo Surgical, Reverse® shoulder prosthesis Surgical Technique, Feb. 2008.
Eclipse™ Stemless Shoulder Prosthesis, Surgical Technique Guide, Anthrex GmbH, 2014, in 12 pages.
Epoca Shoulder Arthroplasty System, Synthes, Inc., Apr. 2008, in 4 pages.
Epoca Shoulder Arthroplasty System—Stem and Glenoid Technique Guide, Synthes, Inc., Apr. 2008, in 56 pages.
Innovative Design Orthopaedics, "Verso® Shoulder Surgical Technique", 2013.
Kany et al., "A convertible shoulder system: is it useful in total shoulder arthroplasty revisions?" International Orthopaedics, published online Oct. 16, 2014, vol. 39, pp. 299-304.
Katz et al., "New design of a cementless glenoid component in unconstrained shoulder arthroplasty: a prospective medium-term analysis of 143 cases," published online Oct. 27, 2012, vol. 23, pp. 27-34.
Montoya et al., "Midterm results of a total shoulder prosthesis fixed with a cementless glenoid component," Journal of Shoulder and Elbow Surgery, May 2013, vol. 22, Issue 5, pp. 628-635.
SMR Axioma® TT Metal Back Surgical Technique, Product Brochure, Lima Corporate, dated Sep. 2013, in 48 pages.
Taunton et al., "Total Shoulder Arthroplasty with a Metal-Backed, Bone-Ingrowth Glenoid Component," The Journal of Bone and Joint Surgery, Oct. 2008, vol. 90-A, Issue 10, pp. 2180-2188.
Teissier et al., "The TESS reverse shoulder arthroplasty without a stem in the treatment of cuff-deficient shoulder conditions: clinical and radiographic results," Journal of Shoulder and Elbow Surgery, Jan. 2015, vol. 24, Issue 1, pp. 45-51.
The Anatomical Shoulder™: A true system approach, Product Brochure, Zimmer UK Ltd, printed 2006, in 6 pages.
Univers Revers™ Total Shoulder System, Surgical Technique Guide, Anthrex Inc., Version D, revised Jul. 2, 2015, in 28 pages.
International Search Report and Written Opinion issued in PCT Application No. PCT/US2020/045211, dated Dec. 17, 2020, in 18 pages.
International Search Report and Written Opinion issued in connection with International Patent Application No. PCT/US2022/080550, dated Apr. 10, 2023, 16 pages.
Extended European Search Report issued in connection with European Patent Application No. 22201630.5, dated Feb. 9, 2023, 8 pages.
Non-Final Office Action issued in connection with U.S. Appl. No. 17/149,308, dated May 23, 2023, 12 pages.
Second Office Action issued in connection with Japanese Patent Application No. 2022-507908, dated Jun. 20, 2023, 7 pages.

* cited by examiner

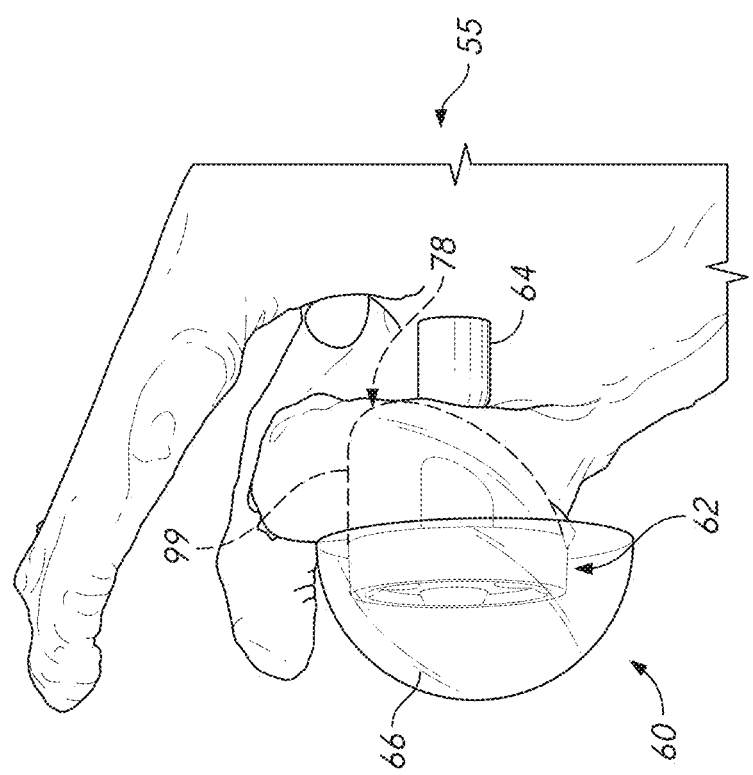
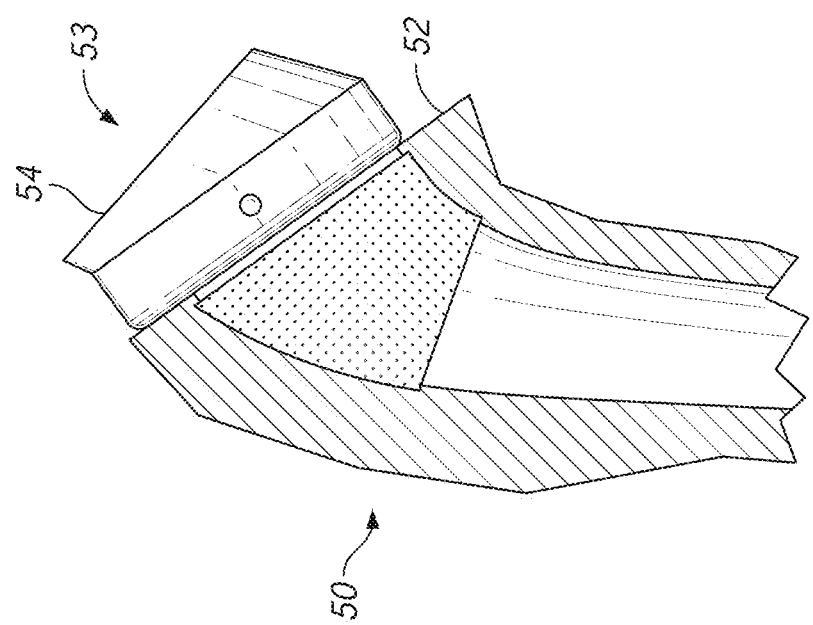
FIG. 1

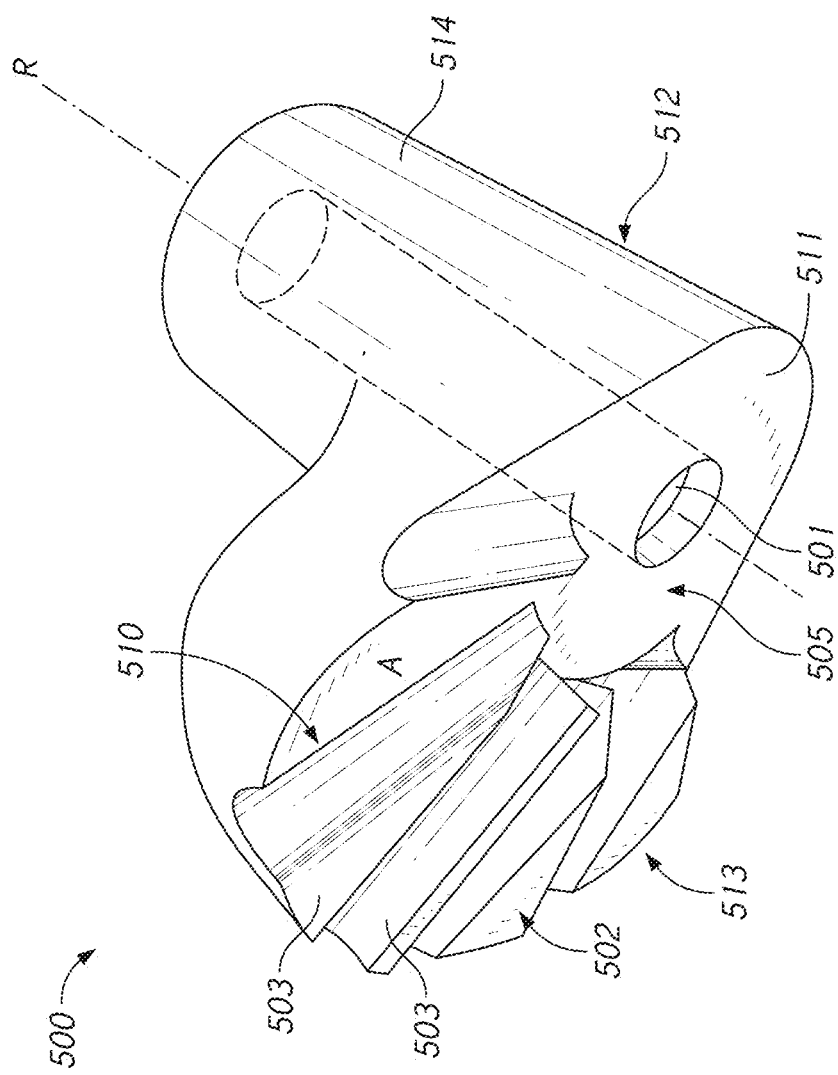

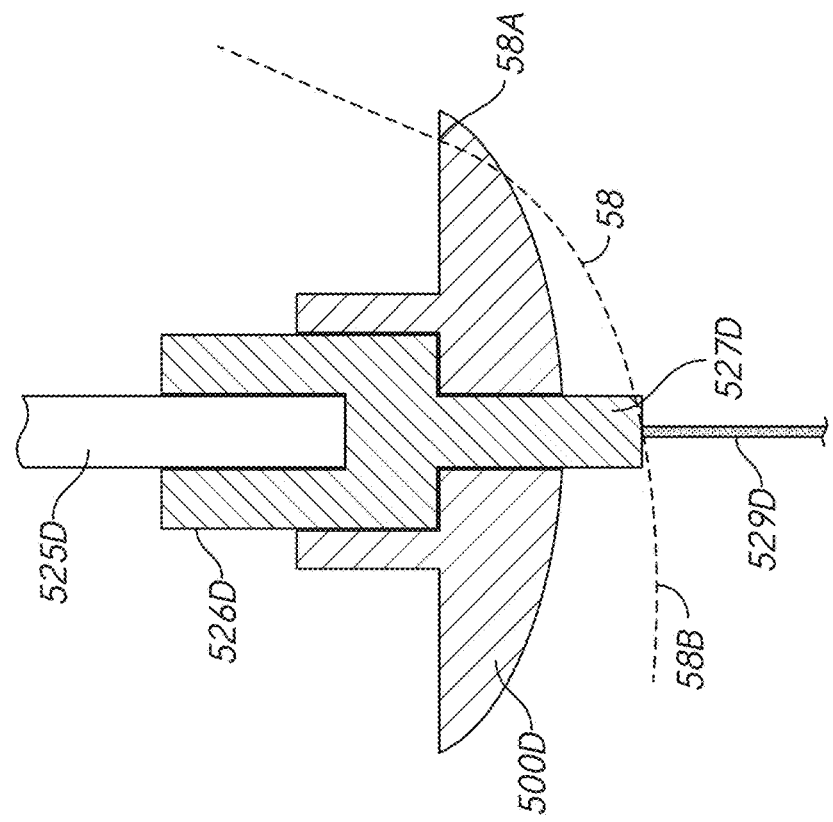
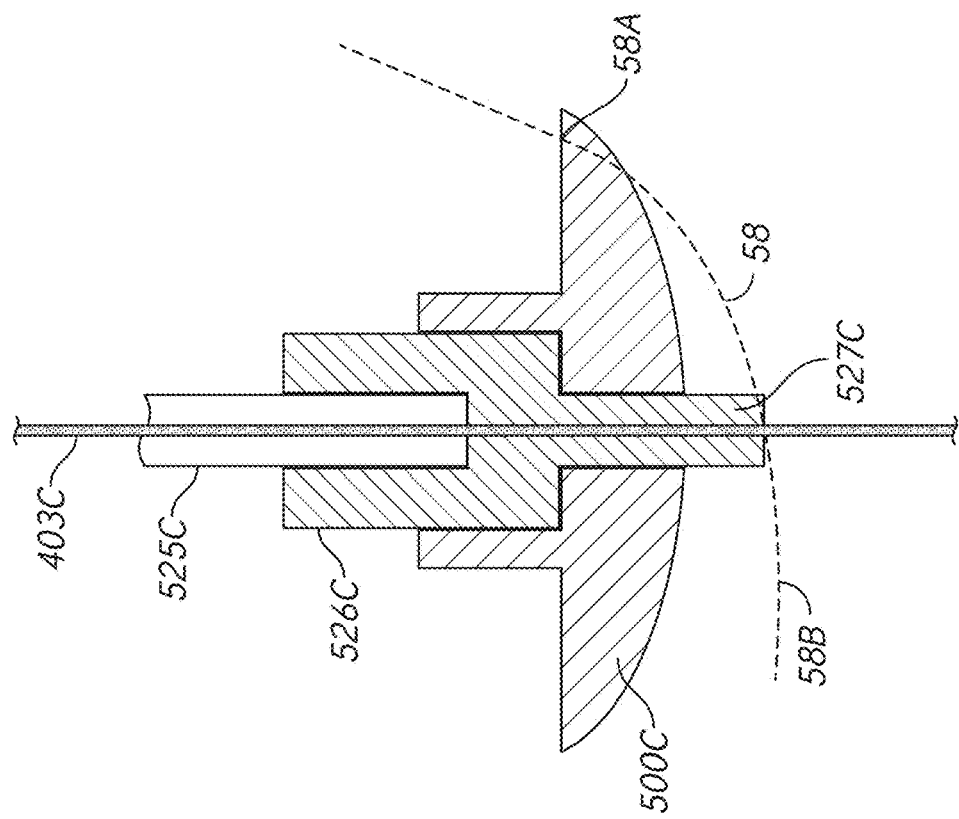
FIG. 5K
FIG. 5J

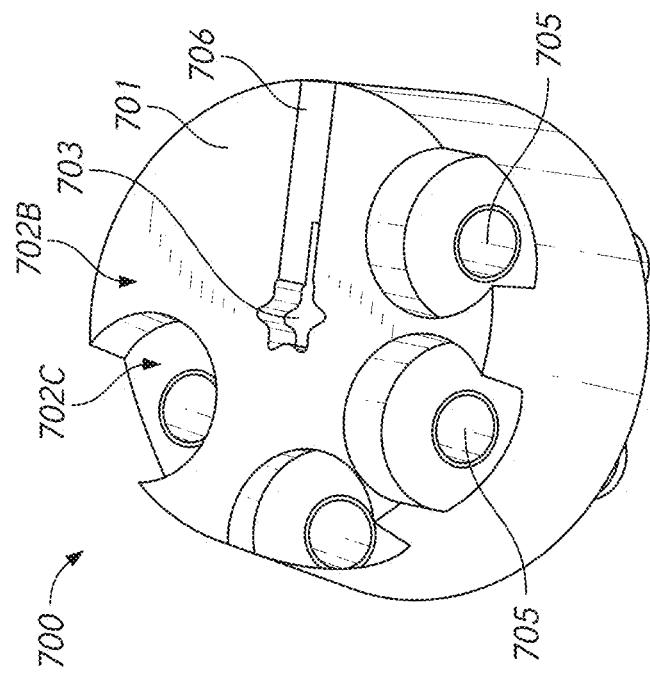
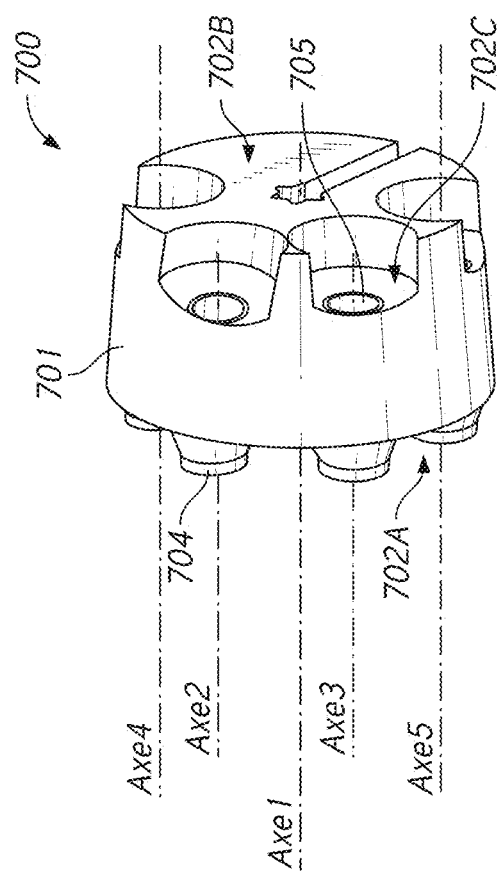
FIG. 8B
FIG. 8A

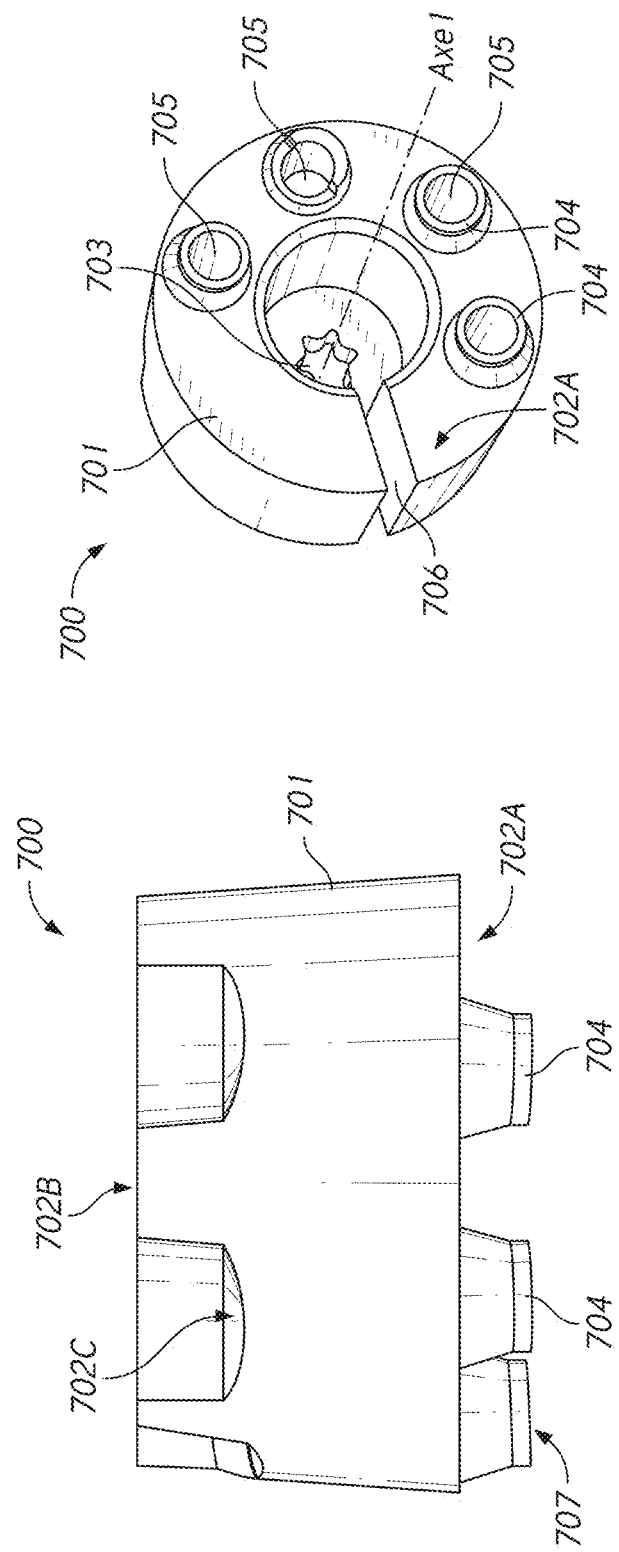

APPARATUSES AND METHODS FOR IMPLANTING GLENOID PROSTHESES

CROSS REFERENCE TO RELATED APPLICATIONS

This application is a Continuation-In-Part of International Patent Application PCT/US2020/045211, filed Aug. 6, 2020, which claims the benefit of U.S. Provisional Patent Application No. 62/885,033, filed Aug. 9, 2019, which are incorporated herein by reference.

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 C.F.R. § 1.57.

BACKGROUND OF THE INVENTION

Field of the Invention

This application is directed to apparatuses and methods for improved preparation of a glenoid region of a scapula in connection with implantation of a shoulder prosthesis and to apparatuses that can be implanted following use of such apparatuses and methods.

Description of the Related Art

Shoulder joint conditions can sometimes be resolved with shoulder arthroplasty. More and more, efforts are being focused on making total shoulder joint arthroplasty available to patients who would benefit from such treatment. In a total shoulder joint arthroplasty, the glenoid is typically reamed and a glenoid articular component is mounted to the scapula following reaming. The articular component provides a smooth surface for movement of a humeral head or humeral articular component.

A glenoid baseplate can be used to support the glenoid articular component on the scapula. The glenoid baseplate can include an anchor peg on the medial side thereof that is configured to be inserted into scapular bone as part of securing the glenoid baseplate to the scapula.

SUMMARY OF THE INVENTION

Apparatuses and methods for improved glenoid preparation are needed to improve the placement of glenoid baseplates. For example, apparatuses and methods disclosed and claimed herein can improve glenoid preparation by reducing the amount of bone removed prior to implanting a glenoid baseplate. Also, apparatuses and methods disclosed and claimed herein can improve glenoid preparation by providing flexibility in the location of an anchor peg of the baseplate, e.g., at or spaced from a central position of the glenoid of a particular patient. Apparatuses and methods disclosed and claimed herein can improve glenoid preparation by allowing a particular patient to benefit from reduced, minimal or no reaming in one region of a glenoid and to allow a surgeon to ream another region of the glenoid such as to remove obstructive osteophytes or other problematic bone formations. Additional improvements over the prior art are described and claimed herein below.

In one embodiment, a method for performing shoulder surgery is disclosed. The method can include guiding a guide pin into the glenoid surface along a reaming axis. The method can include placing a partial reaming guide in contact with the glenoid surface over the guide pin. A reamer can be advanced over the guide pin to ream the glenoid surface. The reamer can be further advanced over the guide pin until the reamer contacts the partial reaming guide, whereby such contact limits reaming to only a portion of the glenoid surface.

In some embodiments, the method can include forming a channel in the scapula medially from the glenoid surface, the channel configured to receive an anchor peg of a glenoid baseplate. A drill can be advanced over the guide pin to form an anchor peg channel centered on the reaming axis. The method can include advancing an anchor peg channel forming guide toward the glenoid surface, the anchor peg channel forming guide comprising a body and an aperture formed inward of a periphery of the body and securing the anchor peg channel forming guide against the glenoid surface with the aperture off-set from the reaming axis. In some embodiments, advancing the reamer and further advancing the reamer comprises reciprocating a reaming surface of the reamer about an angle of less than 180 degrees relative to the reamer axis. In various embodiments, the method can further include inserting an anchor peg of a glenoid baseplate into an anchor peg channel formed in the glenoid surface. A screw trajectory guide can be coupled with the baseplate and one or more screw holes can be formed in the scapula through the screw trajectory guide and the baseplate. A depth of the one or more screw holes can be controlled with a corresponding depth control surface of the screw trajectory guide. The method can further include defining a reaming axis based on image data responsive to a scan of a scapula of a patient.

In another embodiment, a kit for shoulder surgery is disclosed. The kit can include a partial reaming guide having a patient-matched surface shaped to conform to a scapula of a patient. The partial reaming guide can be configured to limit glenoid reaming about a reaming axis to only a portion of a glenoid. The kit can include an anchor peg channel guide having a patient-matched surface shaped to conform to a portion of the glenoid. The anchor peg channel guide can have a channel offset from the reaming axis.

In some embodiments, the kit can include a screw trajectory guide having a protrusion shaped to be inserted into an aperture of a glenoid baseplate, the protrusion including a channel extending therethrough. The kit can include a glenoid baseplate having an anchor member. The kit can include a three-dimensional (3D) model of the scapula of the patient. The kit can include an alignment guide having a plurality of contact members configured to conform to a plurality of surfaces of a scapula, the alignment guide comprising an aperture configured for placing a guide wire in the glenoid. The anchor peg channel guide can have a portion configured to rest on the reamed portion of the glenoid. The kit can include a reaming device comprising a stop surface and a reaming portion having one or more reaming features configured to ream a bone surface. The reaming device further can include a guide hole through the reamer body, the guide hole sized and shaped to receive a guide pin therethrough. The reaming portion can include an arc-shaped structure that delimits an angle less than 180 degrees. The reaming device can include a first lower portion which comprises the reaming portion and a second upper portion angled relative to the lower portion, the guide hole formed through the second upper portion.

In another embodiment, a partial reaming guide for use in a shoulder treatment procedure is disclosed. The partial reaming guide can include a guide body comprising a patient-matched surface shaped to conform to a portion of a scapula of a patient. The partial reaming guide can include a reamer depth stop surface at a first height above the patient-matched surface, the reamer depth stop surface positioned to serve as a depth stop for the reaming device to control a depth of reaming. The partial reaming guide can include a first hole through the guide body extending from the reamer depth stop surface to the mounting surface, the first hole aligned with a reaming axis.

In some embodiments, the guide body can include a raised surface at a second height greater than the first height, a second hole extending through the guide body from the raised surface to the patient-matched surface. The guide body can include a receiver body defined between the raised surface and the mounting surface. A second hole can be formed through the guide body offset from the first hole, the second hole to rotationally orient the guide body relative to the scapula.

In another embodiment, an anchor peg channel guide for use in a shoulder treatment procedure is disclosed. The anchor peg channel guide can include a guide body comprising a patient-matched surface shaped to conform to a scapula of a patient and a lateral surface opposite the mounting surface. The anchor peg channel guide can include a channel disposed through the guide body, the channel positioned to be offset from a reaming axis of the scapula. The guide body can include a rotational alignment hole through the guide body.

In some embodiments, a center of a periphery of the guide body of the anchor peg channel guide can be spaced apart from a center of the channel. At least one peripheral hole can be provided for securing the guide body to the scapula.

In another embodiment, a screw trajectory guide for use in a shoulder procedure is disclosed. The screw trajectory guide can include a guide body having a first surface shaped to mate with a glenoid baseplate, a second surface opposite the first surface, and a third surface recessed from the second surface between the first and second surfaces. The guide body can include a protrusion extending from the first surface and shaped to be inserted into corresponding apertures of the glenoid baseplate. The guide body can include a channel extending from the third surface through the protrusion to a distal end of the protrusion.

In some embodiments, a guide channel can be formed through the guide body, the guide channel to receive a guide wire therethrough. A slot can extend from the guide channel to an outer periphery of the guide body. A plurality of protrusions can extend from the first surface and be shaped to be inserted into corresponding apertures of the glenoid baseplate. A plurality of channels can also be provided, with each channel extending from one of a plurality of third surfaces through a corresponding one of a plurality of protrusions. At least one of the third surfaces can be disposed at an elevation that is prescribed for the patient to control a depth of a peripheral screw hole formed in a scapula through the channel extending from the at least one third surface.

In another embodiment, a reamer for use in shoulder surgery is disclosed. The reamer can include a reamer body comprising a stop surface and a reaming portion having one or more reaming features configured to ream a bone surface. The reamer can include a guide hole through the reamer body, the guide hole sized and shaped to receive a guide pin therethrough. The reaming portion can comprise an arc-shaped structure that delimits an angle less than 180 degrees.

In some embodiments, the reamer body can include a first lower portion through which comprises the reaming portion and a second upper portion angled relative to the lower portion, the guide hole formed through the second upper portion.

In one embodiment, a method for performing shoulder surgery is disclosed. The method can include guiding a guide pin into the glenoid surface along a reaming axis; selecting a tip connector based on patient-specific image data; connecting a reaming device to a handle by way of the selected tip connector; and advancing the reaming device over the guide pin to at least partially ream the glenoid surface.

In some embodiments, the method can include after the advancing, placing a guide pin guide over the at least partially reamed glenoid surface to verify the at least partial reaming, the guide pin guide having a patient-matched bone-facing surface. In some embodiments, the method can include installing a glenoid assembly in the glenoid surface after the advancing. In some embodiments, selecting the tip connector comprises selecting the tip connector from a plurality of differently-sized tip connectors. In some embodiments, selecting the tip connector comprises forming the tip connector based on the patient-specific image data.

In another embodiment, a reaming instrument can include a reamer shaft; a reaming device; and a tip connector that connects the reaming device to the reamer shaft, the tip connector having a projection that extends distal a distal-most surface of the reaming device.

In some embodiments, the reaming instrument can include an opening through the reaming device and the tip connector, the opening sized to receive a guide pin. In some embodiments, the reaming instrument can include a plurality of tip connectors with distally-extending projections having different lengths. In some embodiments, the tip connector comprises a second projection extending distally from the projection, a diameter of the second projection smaller than a diameter of the projection. In some embodiments, a kit can comprise the reaming instrument, a first guide pin guide having a surface that is matched to a patient's native bone structure, and a second guide pin guide having a surface that is matched to a reamed portion of the patient's glenoid. In some embodiments, the kit can include a glenoid assembly including a glenoid baseplate and an articular body supported by the glenoid baseplate.

BRIEF DESCRIPTION OF THE DRAWINGS

Various embodiments are depicted in the accompanying drawings for illustrative purposes, and should in no way be interpreted as limiting the scope of the embodiments. Furthermore, various features of different disclosed embodiments can be combined to form additional embodiments, which are part of this disclosure.

FIG. 1 shows a model of a human humerus and a scapula with a glenoid, the glenoid having an articular assembly coupled thereto, the articular assembly including a glenoid baseplate with a medial end that projects through a posterior wall of the scapula, the humerus having a reverse implant assembly coupled thereto;

FIG. 5A is a bottom perspective view of the reamer illustrated in FIG. 5;

FIGS. 5I-5K illustrate example reaming instruments, according to various embodiments;

FIG. 8A is a lateral side perspective view of the peripheral screw trajectory guide of FIG. 8 illustrating various peripheral screw trajectories;

FIG. 8B is a lateral side perspective view of the peripheral screw trajectory guide of FIG. 8 showing a slot feature for removal of the guide;

FIG. 8C is a side view of the peripheral screw trajectory guide of FIG. 8 showing depth stop surfaces and baseplate mating protrusions disposed on a medial side;

FIG. 8D is a medial side perspective view of the peripheral screw trajectory guide of FIG. 8 showing a baseplate mating channel formed therein.

DETAILED DESCRIPTION OF THE PREFERRED EMBODIMENT

Figure 1A:
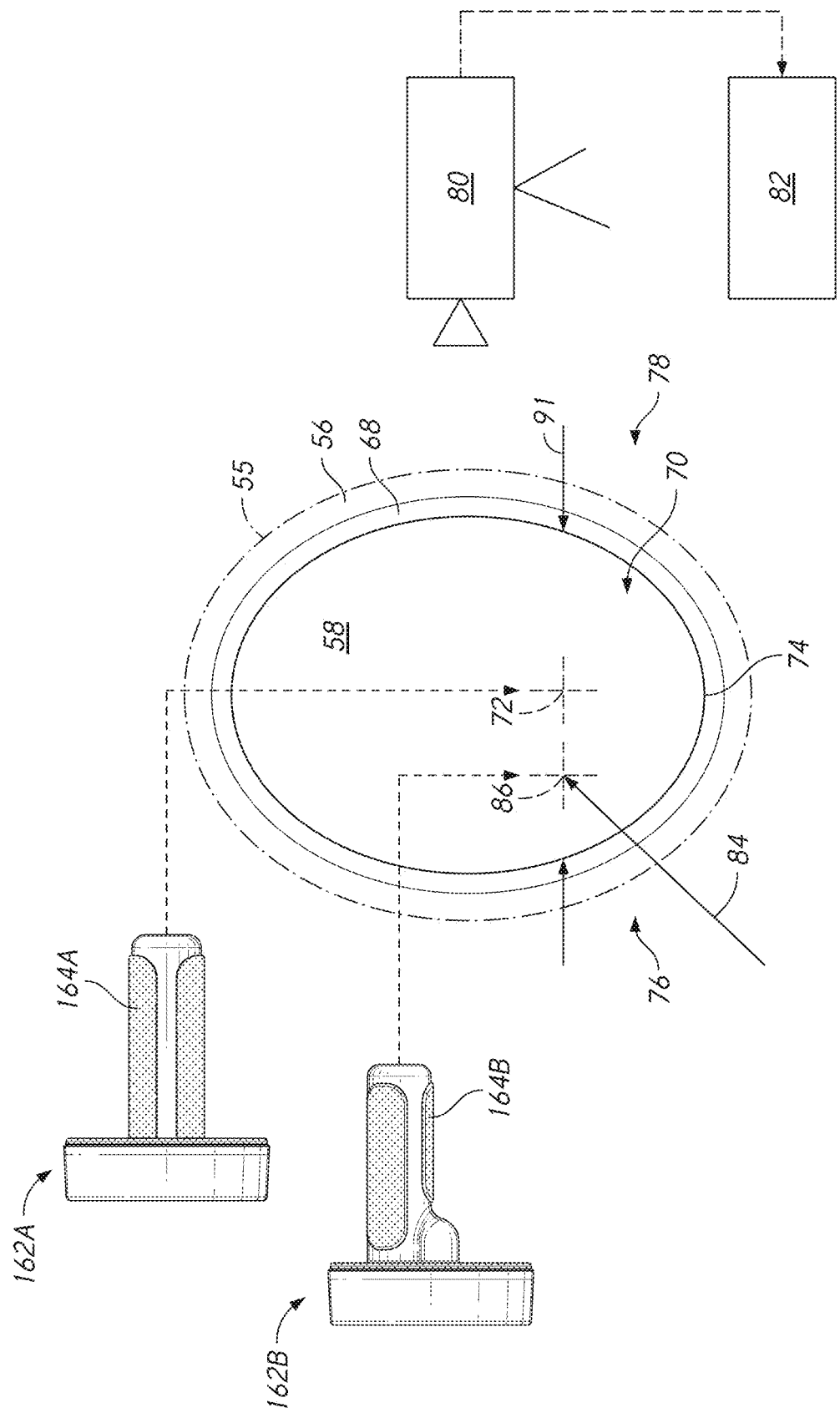
FIG. 1A is a schematic view of a glenoid and an imager that can be used to gather imaging information pertaining to the glenoid and of two example baseplates that can be selected, designed and/or manufactured based on analysis of such imaging information.

This application is directed to improving the success in providing sound connection between a glenoid assembly and a human scapula. These improvements are intended to allow for greater success in shoulder arthroplasty surgery. These improvements also allow a surgeon, engineer or other personnel involved in implementing a surgical treatment to optionally position a baseplate anchor peg centrally or eccentrically and also to determine whether to implement a surgery with some reaming, e.g., to remove osteophytes or other obstructive bone, while still providing a baseplate medial surface that is at least partially patient matched to reduce, minimize or eliminate reaming for such portions.

FIG. 1 illustrates concerns that can arise in some shoulder procedures, showing a humerus 50 and a scapula 55 of a shoulder having reverse shoulder implants disposed therein. The humerus 50 has a humeral resection 52. A humeral implant assembly 53 including a humeral anchor (shown beneath the humeral resection 52) and a reverse articular body 54. The reverse articular body 54 can be disposed above the humeral resection 52. The reverse articular body 54 can be at least partially below the humeral resection 52. The scapula 55 has a glenoid, which is the portion of the scapula 55 on which the head of the humerus 50 normally articulates. Following reverse shoulder arthroplasty, this function is provided by an articular body 66 that is coupled to the scapula 55. A glenoid assembly 60 can be provide that includes a glenoid baseplate 62 to support the articular body 66. The glenoid baseplate 62 can be coupled with the scapula 55. The glenoid baseplate 62 can have an anchor peg 64 configured to be advanced into the scapula 55. The glenoid baseplate 62 can be placed on the glenoid without or with minimal reaming. The glenoid baseplate 62 can be placed on the glenoid with partial reaming, using apparatuses and methods described herein.

In a sub-optimal case, the glenoid baseplate 62 is not properly placed on the scapula 55. FIG. 1 shows that the anchor peg 64 of the glenoid baseplate 62 can be placed into the scapula 55 in a sub-optimal manner in which a medial end of the anchor peg 64 pierces the posterior surface 78 of the scapula 55. The anchor peg 64 can be exposed outside the scapula 55 in that case. This outcome is sub-optimal for several reasons. The security of the connection between the anchor peg 64 and the bone of the scapula 55 is a function of the length over which there is direct contact between these structures. The direct contact provides opportunities for bony ingrowth, providing security. No such ingrowth will occur along a length that is completely exposed. Further, an exposed end could cause irritation to soft tissue around the scapula 55. Further, if the anchor peg 64 were to perforate the bone in an undesirable location the perforation could weaken the scapula and increase the risk of fracture.

FIG. 1A shows a schematic of a lateral side of a scapula 55. The glenoid 58 includes an articular surface separated from the rest of the glenoid 58 by a glenoid rim 68. A healthy shoulder joint will generally have within the glenoid rim 68 an elongate articular surface that has a generally circular inferior portion 70. More particularly the inferior portion 70 can be bounded by a circular segment of the glenoid rim 68. The circular portion of the glenoid rim 68 can be disposed about a center 72. More generally, the center 72 can be a central portion, e.g., a geometric center, of the inferior portion 70. The center 72 can be disposed on or along a infero-superior axis of the glenoid rim 68 that extends from the superior-most portion (located at the top of the graphic in FIG. 1A) of the glenoid rim 68 to the inferior-most portion (located at the bottom in FIG. 1A) of the glenoid rim 68. The center 72 may be located at a central portion, e.g., a mid-point, of a chord extending across the glenoid rim 68 at an infero-superior position disposed inferior of a geometric center of the entire glenoid 58 or glenoid rim 68. For example, the center 72 can be located about one-half to two-thirds of the distance from the inferior-most point of the glenoid rim 68 to the geometric enter of the entire glenoid 58 or glenoid rim 68.

As will be discussed in greater detail below, an imager 80 can be used to scan the scapula 55 to gather imaging information. That information can be processed in an image processing system 82. The image processing system 82 can include a memory that can store imaging information corresponding to scanned data from the imager 80. The image processing system 82 can also include one or more hardware processors that can execute instructions. The image processing system 82 can process the imaging information to identify all the foregoing structures of the scapula 55. The imaging information can also be processed to locate an anchor trajectory 84 in a direction into the scapula 55 for placement of an anchor peg. The anchor trajectory 84 can be offset from the center 72 of an inferior portion 74 of a glenoid 58. As shown in FIG. 1A the offset can be in the direction of the anterior surface 76. The anchor trajectory can be at a center 86 of an opening that can be located between the center 72 and the anterior surface 76. The center 86 can be located 10% of the distance from the center 72 to the anterior aspect of the glenoid rim 68 adjacent to the anterior surface 76 of the scapula 55. The center 86 can be located 20% of the distance from the center 72 to the anterior aspect of the glenoid rim 68 adjacent to the anterior surface 76 of the scapula 55. The center 86 can be located 30% of the distance from the center 72 to the anterior aspect of the glenoid rim 68 adjacent to the anterior surface 76 of the scapula 55. The center 86 can be located 40% of the distance from the center 72 to the anterior aspect of the glenoid rim 68 adjacent to the anterior surface 76 of the scapula 55. The center 86 can be located 50% of the distance from the center 72 to the anterior aspect of the glenoid rim 68 adjacent to the anterior surface 76 of the scapula 55. The center 86 can be located 60% of the distance from the center 72 to the anterior aspect of the glenoid rim 68 adjacent to the anterior surface 76 of the scapula 55. In some cases, the center 86 is located in a direction other than toward the anterior surface 76, e.g., closer to the posterior surface 78 of the scapula 55 by any of these or other percentages. The center 86 could be in other directions as well, e.g., inferior, superior, or some direction between any of anterior, posterior, inferior, or superior depending on the needs of the patient.

FIG. 1A shows that a patient process flow can enable one to select between a first baseplate 162A with a centrally positioned anchor peg 164A and a second baseplate 162B with an off-set anchor peg 164B. The first baseplate 162A is suitable for placement at the center 72, e.g., when the bone beneath the center 72 has sufficient depth to allow the anchor peg 164A of the first baseplate 162A to be enclosed in a blind hole formed in the scapula 55 beneath the center 72. The second baseplate 162B is suitable for placement at the center 86, e.g., when the bone beneath the center 72 does not have sufficient depth but that bone beneath the center 86 has sufficient depth to allow the anchor peg 164B of the second baseplate 162B to be enclosed in a blind hole formed in the scapula 55 beneath the center 86.

Figure 1B:
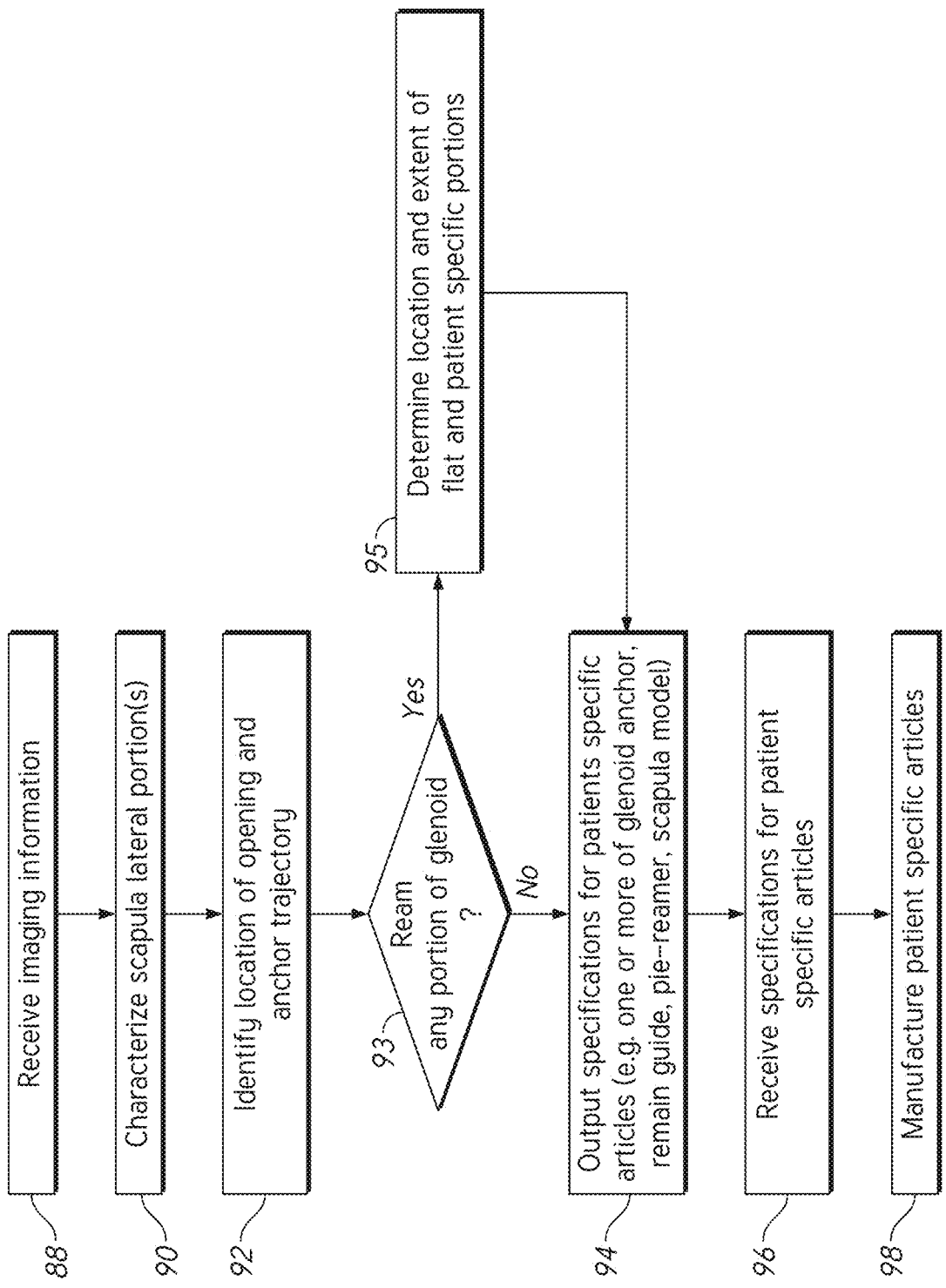
FIG. 1B is a flow chart of a method that can be performed with imaging information.

The image processing system 82 can be configured to process imaging information in any suitable manner. FIG. 1B shows one method that can be performed at least in part by the image processing system 82. In a step 88 a process can receive the imaging information. For example, the imager 80 can be connected by a network to a computer having a processor configured to receive the imaging information. The network can include an Internet connection, a wireless or wired connection within the same facility where the imager 80 is located. In some applications, a data file including the imaging information can be physically transported to an image processing computer. In some applications, the imager 80 is directly connected to a computer with a processor configured to process the imaging information.

Thereafter in a step 90 a lateral portion or surface 56 of a scapula 55 can be characterized. The characterization of the lateral portion can include segmentation to create a virtual model of all or a portion of the scapula 55. The step 90 can include forming a virtual model of all or a portion of the humerus 50. The step 90 can include forming a virtual model of all or a portion of the glenoid 58. A virtual model formed in step 90 can include a model of the glenoid rim 68. The virtual model formed in step 90 can include a model of an inferior portion 70 of the glenoid rim 68. In step 90, the center 72 of the inferior portion 70 can be identified in the virtual mode. The glenoid 58 can be characterized to locate the center 72, e.g., by obtaining a radius of curvature of the inferior portion 70. The center 72 can be identified as the center for a radius of curvature of the inferior portion 70.

The step 90 can include characterizing a lateral surface 56 of the scapula 55. The scapula 55 can be disposed in the immediate vicinity of the glenoid 58, e.g., in lateral facing bone disposed around the glenoid 58. In some cases, the scapula 55 is further characterized medially of the lateral surface 56, e.g., along an anterior surface 76 and/or along a posterior surface 78 of the scapula 55. The step 90 can include determining the thickness of the scapula 55 between the anterior surface 76 and the posterior surface 78 at one or more locations of the glenoid 58. For example, thicknesses or depth of bone beneath the glenoid 58 can be determined as a measurement between the surface of the glenoid and an external wall of one of the anterior and posterior surfaces 76, 78 beneath any point of the glenoid. The depth may be determined relative to the length of a baseplate anchor peg, e.g., less than or greater than such length.

The step 90 can also include determining a thickness or depth the center 72 and at locations spaced apart from the center 72 if the thickness or depth at the center 72 is not sufficient to fully contain the anchor peg 64 of a glenoid baseplate 62. The step 90 can identify a range of positions for the placement of an anchor peg 64, based on more than one position having sufficient scapula bone depth, thickness or quality.

The image processing system 82 can perform the step 92 in which the location of the center 86 and the anchor trajectory 84 are determined. The image processing system 82 can determine the location of the center 86 by any suitable technique. For example, a hardware processor in the image processing system 82 can execute code implementing a method that determines the thicknesses or depth dimensions for a given location offset from the center 72. At a location disposed an incremental distance anteriorly from the center 72, the image processing system 82 can determine the scapula thickness or depth. If the thickness or depth are sufficient for a given patient, the anchor trajectory 84 as well as the location for the center 86 can be established. If the thickness or depth is not sufficient, a further increment from the center 72 can be evaluated by the image processing system 82. The condition at the bone corresponding to this further increment, e.g., the thickness or depth, can be evaluated by the image processing system 82 to determine if the thickness or depth are sufficient.

In some embodiments the image processing system 82 performs additional steps of the method of FIG. 1B, e.g., to consider whether to further process the glenoid and/or to generate a configuration for a glenoid baseplate 62. The configuration of the glenoid baseplate 62 can include an amount of offset between a center of a proximal or distal (or lateral or medial) portion of the glenoid baseplate 62 and the location of the center of the anchor peg 64. The direction along which the anchor peg 64 extends can be generally perpendicular to a lateral or medial surface of the glenoid baseplate 62 in some embodiments. In some methods, the image processing system 82 concludes the step 92 upon determining the location of the center 86 and the corresponding position of the anchor peg 64 as well as the anchor trajectory 84 within the scapula 55 and the corresponding configuration (e.g., orientation and length) of the anchor peg 64. The opening 86 may advantageously be determined to be located anterior of the center 72 (e.g., using the first baseplate 162A) or offset from the center 72 (e.g., using the second baseplate 162B), e.g., posterior of the center 72, inferior of the center 72, superior of the center 72, or any combination of anterior, posterior, inferior and superior to the center 72 as needed based on the analysis in step 90. FIG. 1A shows that when the direction of the center 86 relative to the center 72 is toward the anterior surface 76, the second baseplate 162B could be used to maintaining a transverse portion of the baseplate 162B centered on the glenoid 58. A range of positions for the center 86 between the center 72 and the posterior surface 78 also can be provided if the posterior surface 78 extends more generally medially-laterally and the anterior surface 76 is more curved toward the posterior surface 78.

In step 93, the image processing system 82 can determine whether any portion of the glenoid 58 is to be reamed. For example, in some patients, it may be preferable to ream a portion of the glenoid 58 in order to prepare a suitable surface (e.g., a flat or planar surface) for implanting a glenoid baseplate. In some embodiments, the image processing system 82 can comprise processing electronics programmed to automatically determine whether any portion of the glenoid 58 is to be reamed. In other embodiments, the clinician can interact with the image processing system 82 to determine whether any portion of the glenoid 58 is to be reamed. If a determination is made that the glenoid 58 is not to be reamed, then the method moves to block 94.

Figure 1C:
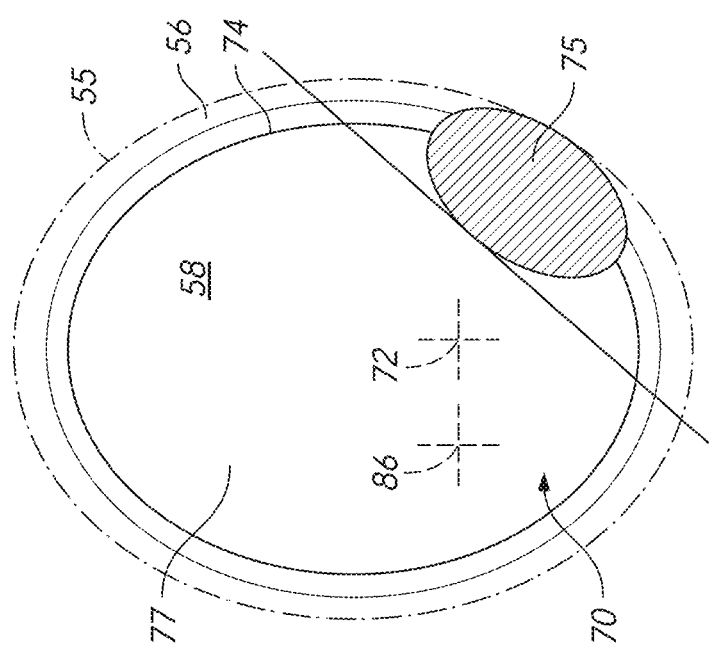
FIG. 1C is a schematic diagram of a portion of a scapula including a glenoid, identifying a portion of the glenoid to be removed prior to implanting a baseplate.

If, however, a determination is made that the glenoid 58 is to be at least partially reamed, then the method moves to a step 95 to determine a location and extend of flat and patient-specific portions of the glenoid 58. As shown in FIG. 1C, for example, the glenoid 58 can include a patient-specific portion 77 which is to remain unreamed and a reamed portion 75 which is to be reamed before inserting the glenoid baseplate. As shown in FIG. 1C, for example, the reamed portion 75 may comprise only a portion of the entire glenoid 58 surface. The reamed portion 75 can be planarized to facilitate implantation of the glenoid baseplate 62 some patients. In some arrangements, the reamed portion 75 can comprise or surround an osteophyte or other obstructive bone growth or formation. The patient-specific portion 77 can be shaped or contoured to match or substantially match the patient's anatomy that is not to be reamed. Once the location and extent of the reamed and patient specific portions are determined, the method can move to the step 94.

In a step 94, a specification or configuration for a glenoid baseplate 62 (e.g., the first or second baseplates 162A, 162B) and for various guides (discussed below in Section I) that can be used to prepare the glenoid 58 and scapula 55 prior to implantation of the baseplate 62 and for glenoid models, various instruments (discussed below in Section I), and other back-table aids (discussed below in Section I) can be output. The output can be in the form of drawings. The output can be computer code to be used by a rapid manufacturing facility. The output in step 94 can be sent directly or indirectly to multiple recipients, including a review recipient, a manufacturing recipient, a physician customer and/or a patient customer.

In step 96 the configuration or specifications output in step 94 can be received by a manufacturing facility. The configuration or specification can be received by other parties in step 96. Step 96 can involve a 3D printer of any sort or another form of additive manufacturing receiving instructions output in the step 94. The instructions can be received and can be implemented by the 3D printer or other additive manufacturing facility forming the glenoid baseplate 62, guides, instruments, and back-table aids, in a step 98. In various embodiments, for example, a reaming axis of a reamer and/or reamer guide can be defined at least in part based on the scan and/or 3D model of the patient's scapula. The step 98 generate the glenoid baseplate 62, guides, instruments, and back-table aids by forming these articles and thereafter putting these articles through appropriate finishing processes. The step 98 can include transferring the glenoid baseplate 62, guides, instruments, and back-table aides to the surgeon immediately upon concluding the method of FIG. 1B or subsequently.

I. Method of Implanting a Glenoid Baseplate

Various embodiments disclosed herein relate to methods and instruments for implanting a glenoid baseplate into a scapula of a patient. The methods and instruments can be used to install guide pins in the glenoid 58 using a guide pin placement guide, to partially ream a portion of the glenoid 58, and to implant the glenoid baseplate 62 into the glenoid. A patient-matched anchor peg forming guide can be used to form an anchor channel for the anchor peg of the glenoid baseplate. A screw trajectory guide can be used to form screw holes in the glenoid baseplate.

A. Partial Reaming Guides

Figure 3:
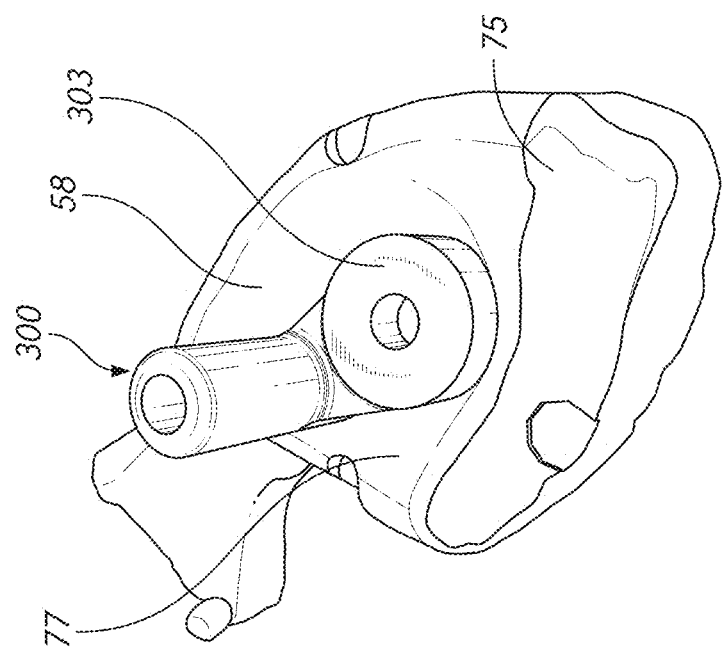
FIG. 3 is a schematic view of a glenoid that has been at least partially prepared for mounting a glenoid baseplate thereto, the preparation including reaming a limited area of the glenoid.
Figure 2:
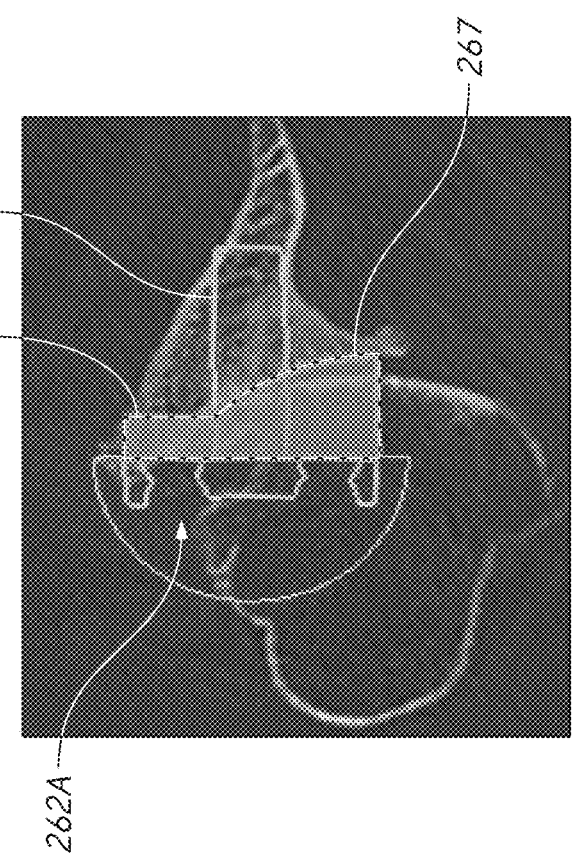
FIG. 2 is a side perspective view of a baseplate having a portion having a patient-matched medial side and a portion configured to mate with a reamed or otherwise modified glenoid bone surface.

As explained above, in some patients, it may be desirable to only partially ream the glenoid 58. FIG. 2 illustrates a glenoid baseplate 262A having an anchor peg 264 extending therefrom. The glenoid baseplate 262A can have a patient-matched portion 267 having a patient-matched medial side and a planar portion 265 configured to mate with a reamed or otherwise modified glenoid bone surface. The patient-matched portion 267 can be formed using the 3D model of the patient's glenoid 58 as discussed above in connection with FIG. 1B. The planar portion 265 can be substantially flat in order to mate with the partially-reamed surface. For example, as shown in FIG. 3, the glenoid 58 can include the partially reamed portion 75 and the unreamed portion 77. Although the portion 77 will not have been reamed it may be modified in the use of the guides disclosed herein such as by being exposed by removing cartilage. As shown, the reamed portion 75 is only a limited portion of the entire glenoid 58. Thus, when implanted, the planar portion 265 can be positioned against the reamed portion 75, and the patient-specific portion 267 can be positioned against the unreamed natural portion 77 of the glenoid 58.

To enable partial reaming of the glenoid 58 shown in FIG. 3, a partial reaming guide 300 can be used to ream only a portion of the patient's glenoid 58. As shown in FIGS. 3-3C, the partial reaming guide 300 can include a guide body 301 including a patient-matched surface 302 shaped to conform to an unreamed portion of the scapula of the patient, such as the unreamed portion 77 of the glenoid 58. The partial reaming guide 300 can comprise a reamer depth stop surface 303 at a first height above the patient-matched surface 302. The depth stop surface 303 is configured to be located at a height that sets the depth at which the reaming device planarizes the reamed portion 75 of the scapula. Thus, the reaming device can have a reaming surface that extends below the depth stop surface 303 and can planarize or ream the scapula to form the reamed portion 75. The reamed portion 75 of the scapula can be below the unreamed portion 77 of the scapula following reaming, as shown in FIGS. 2 and 3. Thus, the reamer depth stop surface 303 can be positioned to serve as a depth stop for the reaming device to control a depth and extent of reaming to ensure that only a portion (e.g., reamed portion 75) is reamed from the glenoid 58. Following the use of the guide 300, the glenoid 58 has the combination of reamed 75 and unreamed surface 77 shown in FIG. 3, as discussed further below.

Figure 3B:
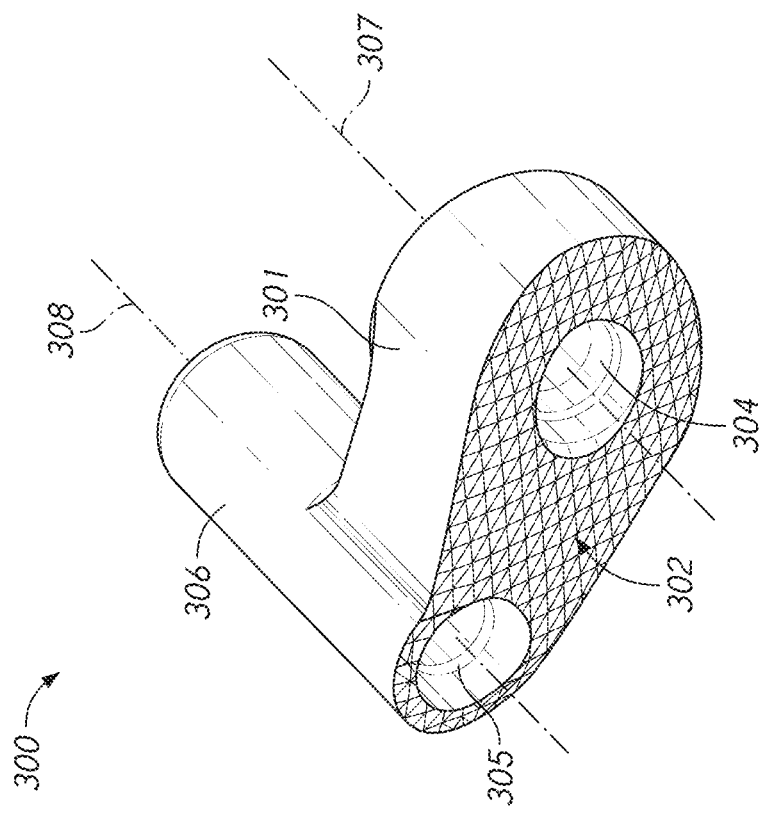
FIG. 3B is a bottom perspective view of the partial reaming guide of FIG. 3A.
Figure 3A:
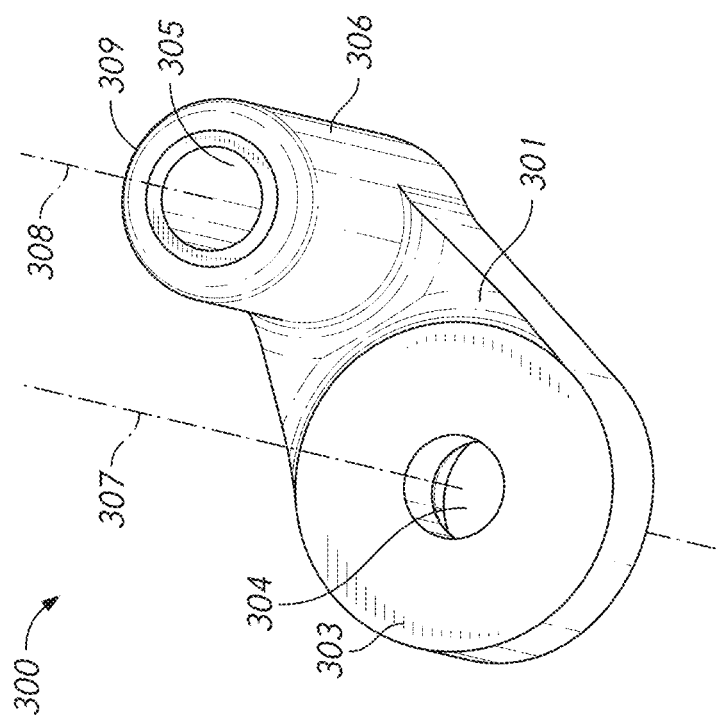
FIG. 3A is a top perspective view of one embodiment of a partial reaming guide having a reamer depth stop disposed on a lateral side thereof.
Figure 3C:
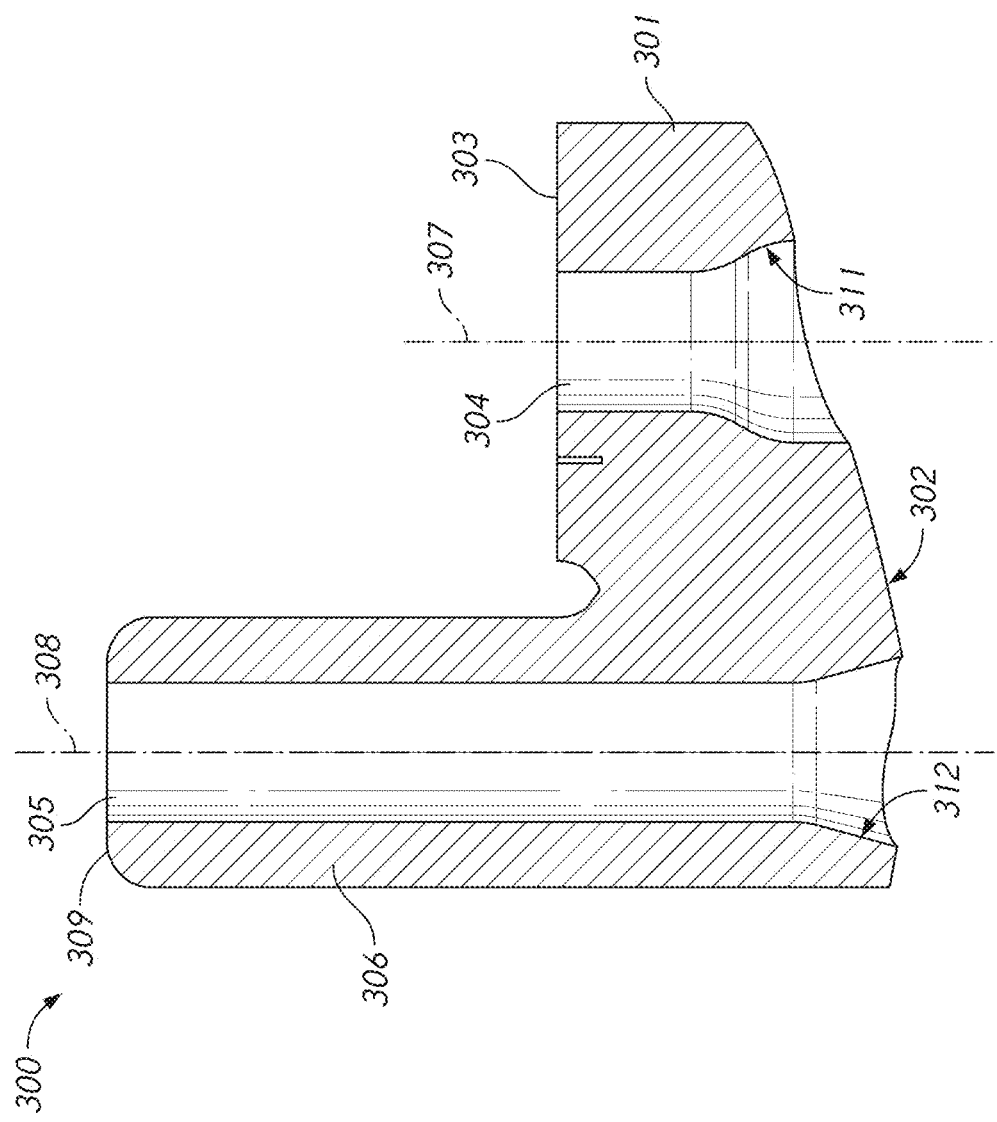
FIG. 3C is a cross-section of the partial reaming guide of FIGS. 3A-3B taking along a plane perpendicular to the reamer depth stop and to longitudinal axes of two holes disposed through the guide.

As shown in FIGS. 3A-3C, a first through hole 304 can be provided in the guide body 301 extending from the reamer depth stop surface 303 to the patient-matched mounting surface 302. The first hole 304 can be aligned with or define a reaming axis 307 about which the reaming device can rotate so as to partially ream the glenoid 58. A receiver body 306, which can comprise a portion of the guide body 301, can extend upwardly from the top surface 303 which also can form a portion of the guide body 301. The receiver body 306 can include a raised surface 309 at a second height. A second hole 305 can extend through the receiver body 306 portion of the guide body 301 from the raised surface 309 to the patient-matched mounting surface 302. The second hole 305 can be offset from the first hole 307 and can be positioned to rotationally orient or align the guide body 301 relative to the scapula of the patient. The second hole 305 can define a rotational alignment axis 308 about which the partial reaming guide 300 can be oriented. The guide body 301 can be advanced over a first guide pin (e.g., guide pin 403 of FIG. 4) through the first hole 304 and a second guide pin (e.g., guide pin 406 of FIG. 4) through the second hole 305. These pins can be aligned or angled to one another in various embodiments. The first and second guide pins can be provided in a manner similar to that explained below in Section I.B.

Moreover, as shown in FIG. 3C, the first hole 304 can comprise a flared or tapered distal surface 311 that flares outwardly towards the patient-matched mounting surface 302. The second hole 305 can comprise a flared or tapered distal surface 312 that flares outwardly towards the patient-matched mounting surface 302. The tapered surfaces 311, 312 can assist in guiding the partial reaming guide 300 over the first and second guide pins by facilitating insertion of the guide pins in the holes 304, 305.

B. Guide Pin Placement Guides

Figure 4:
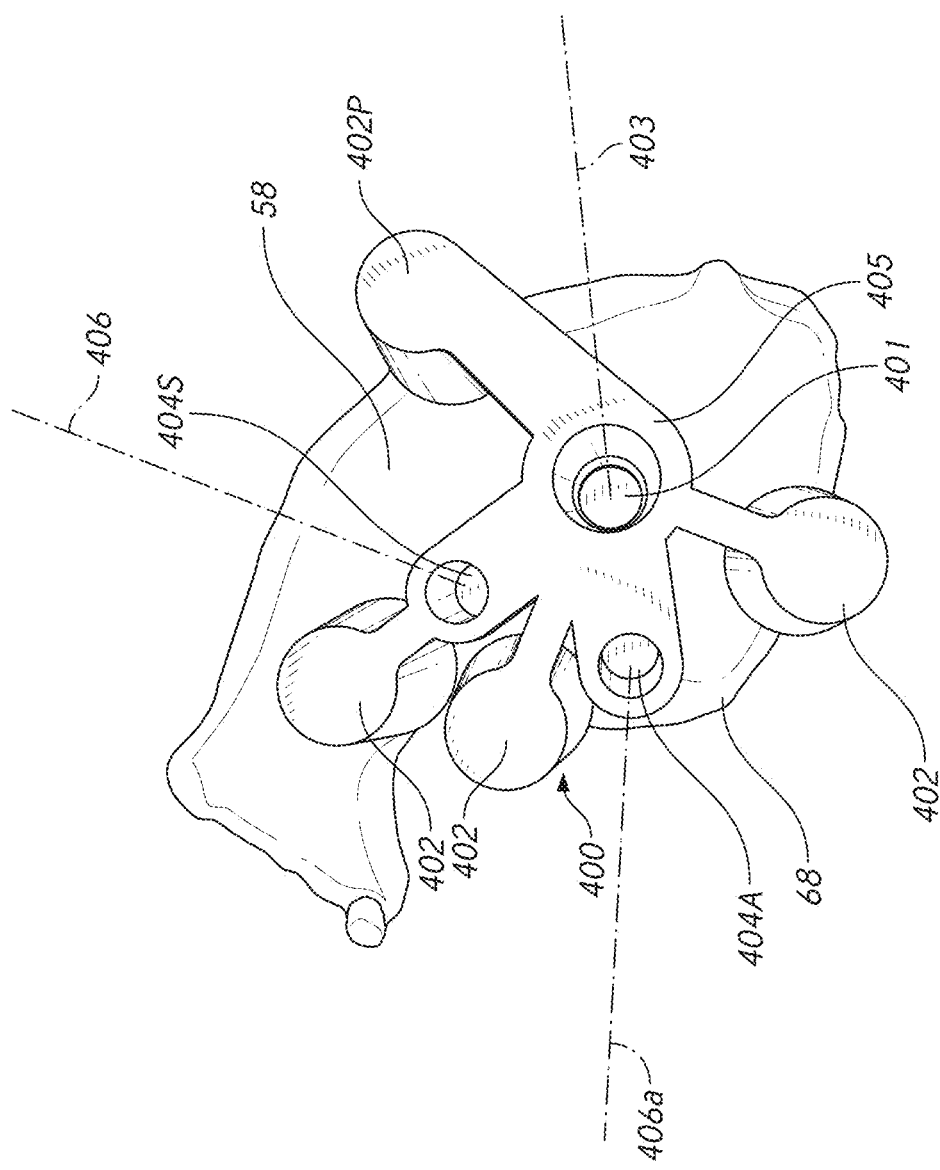
FIG. 4 is a schematic view of a glenoid during a method of preparation of the glenoid, in which a guide pin guide has been placed against a rim of the glenoid and/or portions of the scapula around the glenoid and a guide pin has been placed through a guide pin hole in the guide pin guide.

It can be important to ensure that the instruments used for preparing the glenoid 58 and implanting the glenoid baseplate 62 are accurately aligned with the appropriate portions of the scapula so as to ensure proper implantation of the baseplate 62. FIG. 4 is a schematic view of a glenoid during a method of preparation of the glenoid 58, in which a guide pin guide 400 has been placed against a rim 68 of the glenoid 58 and/or portions of the scapula around the glenoid 58. The guide pin guide 400 can include a central portion 405 and a plurality of contact members, which can be formed as projections or feet 402 extending from the central portion 405. The feet 402 can be patient-matched such that the feet 402 are positioned against the rim 68 of the glenoid 58. Positioning the feet 402 against the rim 68 of the glenoid 58 can help accurately align the guide 400 with the anatomy.

A first opening 401 can be formed through the central portion 405. As shown in FIG. 4, a first guide pin 403 can be placed through the first opening 401, which can serve as a guide pin hole. The first guide pin 403 can be used to guide instruments over the glenoid 58 during preparation of the scapula for implantation with the baseplate. In various embodiments, the first guide pin 403 can be generally aligned with the reaming axis. One or a plurality of second openings 404 (e.g., 404S, 404A) can be disposed through the guide 400. The second opening(s) 404 can be used to rotationally orient the guide 400 and subsequent instruments relative to the glenoid 58 and/or to rotationally secure or otherwise affix the guide 400 to the glenoid during placement of the first guide pin 403. One or more additional guide pins 406, 406a can be inserted into one of the plurality of second openings 404S, 404A, respectively, at locations offset to one another along the scapula to serve as rotational alignment guides for guiding instruments to the scapula. For example, a superiorly located opening 404S immediately adjacent to a contact member 402P disposed on the posterior side of the glenoid 58 can receive the guide pin 406 in one technique. For example, the opening 404S can also be used for placement of the pin 406 as discussed further below in connection with FIGS. 5 and 6. In one embodiment of the guide, the opening 404A can be used for placement of another pin, e.g., the pin 406a as discussed in connection with FIG. 6. Once the guide pin 403 (and/or additional guide pins inserted in the second openings 404) is installed, the guide 400 can be removed from the scapula. The guide pin 403 can remain inserted into the glenoid 58 in order to guide additional instruments to the scapula. The additional guide pins (for example, pins 406 and/or 406a) can also remain inserted into the glenoid 58 to provide rotational alignment for various treatment instruments.

C. Reamer for Partial Reaming

Figure 5:
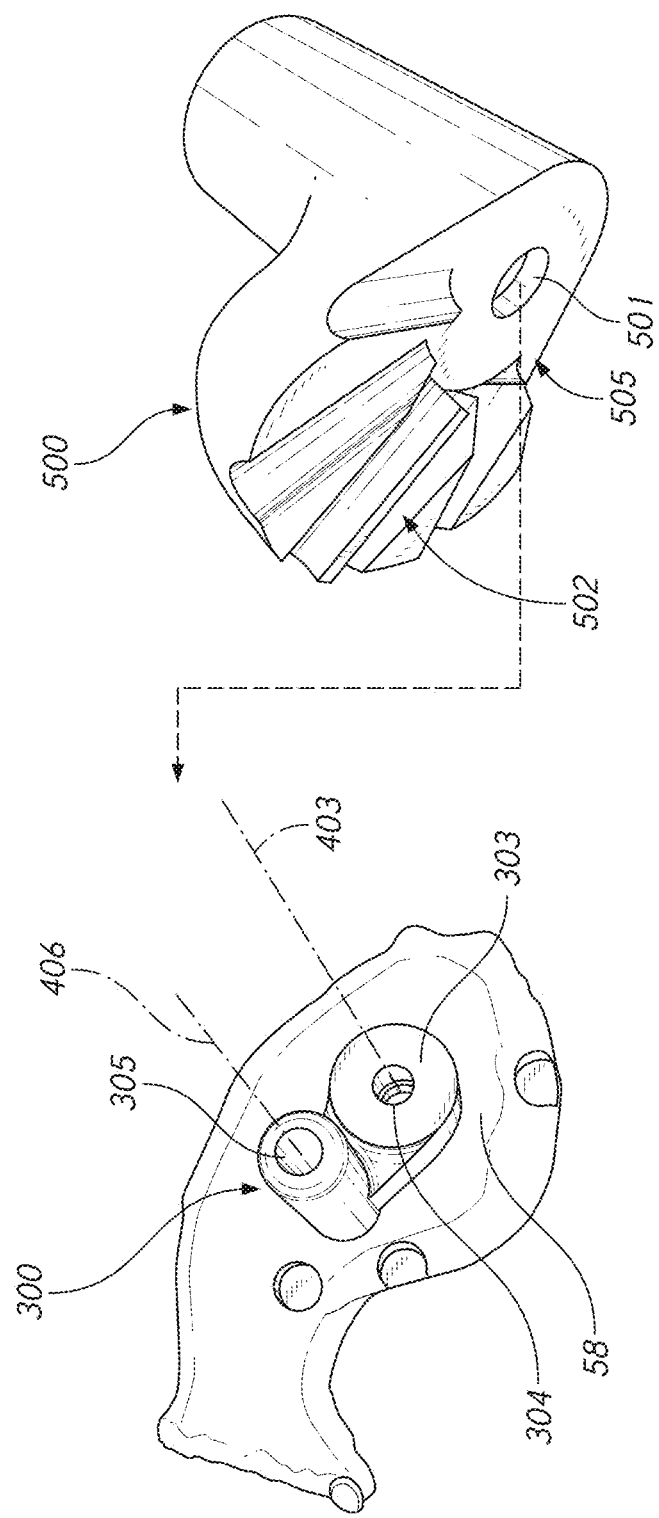
FIG. 5 is a schematic view of a glenoid during a method of preparation of the glenoid, in which the partial reaming guide of FIG. 3A has been advanced over the guide pin placed in the step illustrated in FIG. 4 and further illustrating advancing a reamer of the guide pin toward the depth stop of the partial reaming guide.

As explained above, for some patients, it can be desirable to only partially ream the glenoid 58. In FIG. 5, the partial reaming guide 300 can be placed against the surface of the glenoid 58 with the patient-matched surface 302 (see FIGS. 3A-3C) placed against the glenoid 58. The first hole 304 of the partial reaming guide 300 can be guided over the guide pin 403 and placed against the glenoid 58. In some embodiments, the second hole 305 can be guided along a second guide pin 406. Or, the second guide pin 406 can be placed through the second hole 305 after the guide 300 is placed in contact with the glenoid 58. The guide pin 403 can be disposed along or parallel to a reaming axis R (see FIG. 5A). The second guide pin 406 can be positioned to rotationally align the partial reaming guide 300 at a desired orientation. In some applications, the desired position for the second guide pin 406 is the same as the location of the (or one of the) second openings 404 in the guide 400.

A reaming device 500 (e.g., a pie reamer) can be guided along the guide pin 403. For example, the reaming device 500 can comprise a stop surface 505 and a reaming portion 502 that includes one or more reaming features, such as blades 503 (FIG. 5A). An opening 501 can be provided through the reaming device 500. The opening 501 of the reaming device 500 can be advanced over the guide pin 403 and placed against the scapula. The reaming portion 502 and blades 503 can be placed against the scapula. The reaming device 500 can be rotated about the reaming axis R. To enable partial reaming, the reaming device 500 can be reciprocated about the reaming axis R about an angle of less than 180 degrees relative to the reaming axis R. In some cases, the reaming device 500 can be reciprocated about the reaming axis R about an angle of less than 120 degrees relative to the reaming axis R. In some cases, the reaming device 500 can be reciprocated about the reaming axis R about an angle of less than 90 degrees relative to the reaming axis R. In some cases, the reaming device 500 can be reciprocated about the reaming axis R about an angle of less than 75 degrees relative to the reaming axis R. In some cases, the reaming device 500 can be reciprocated about the reaming axis R about an angle of less than 60 degrees relative to the reaming axis R. In some cases, the reaming device 500 can be reciprocated about the reaming axis R about an angle of less than 45 degrees relative to the reaming axis R. In some cases, the reaming device 500 can be reciprocated about the reaming axis R about an angle of less than 30 degrees relative to the reaming axis R. In some cases, the reaming device 500 can be reciprocated about the reaming axis R about an angle of less than 15 degrees relative to the reaming axis R. The reaming device 500 can be reciprocated and advanced until the stop surface 505 of the reaming device 500 contacts the reamer depth stop surface 303 of the partial reaming guide 300. The reamer depth stop surface 303 of the partial reaming guide 300 and the stop surface 505 of the reaming device 500 can cooperate to ensure that an appropriate depth and extend of the scapula is reamed, based on the patient-specific model of the patient's anatomy. Accordingly, in some applications the reaming device 500 and the reaming guide 300 can be provided to a surgeon together in a kit.

Because the reaming device 500 may be used in combination with the reaming guide 300 it may be advantageous to provide a narrow profile from one side of the device 500 to an opposite side thereof, e.g., from one end of the blades 503 to another end of the blades. More particularly, the blades 503 can be oriented along an arc A that delimits an arc angle and is disposed from a first side 510 of a lower first portion 511 of a body 512 of the device 500 to a second side 513 thereof. The lower first portion 511 can be oriented transverse to an upwardly extending second portion 514 of the body 512. An angle of the arc A between the first side 510 and the second side 513 can be small, e.g., between 10 and 90 degrees, e.g., about 20 degrees, about 30 degrees, about 40 degrees, about 50 degrees, etc.

The upwardly extending second portion 513 of the body 512 can act as a handle for rotating the reaming device 500 about the reaming axis R. In some cases, the reaming device 500 is coupled with or can be part of a driver that can be engaged to oscillate the reaming device 500 by action of a motor or other mechanism.

D. Examples of Reaming Procedures

Figure 5D:
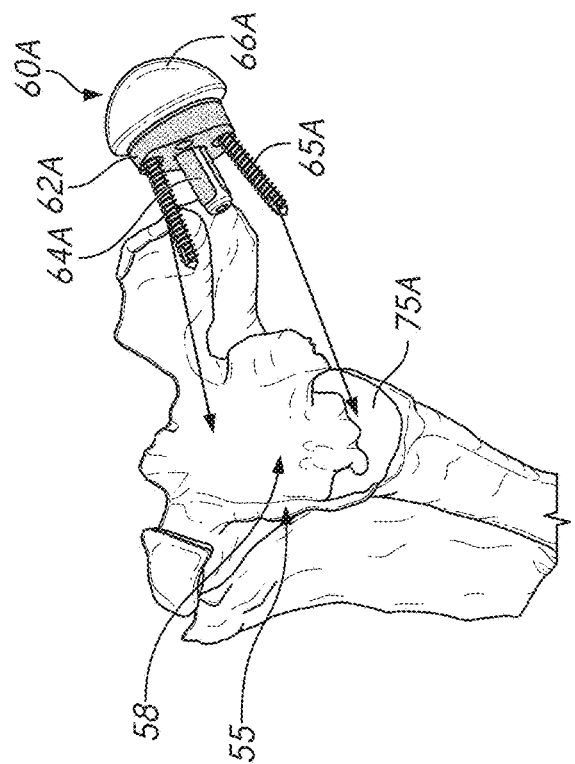
FIGS. 5B-5D illustrate an example method of reaming a portion of a scapula, according to various embodiments.
Figure 5B:
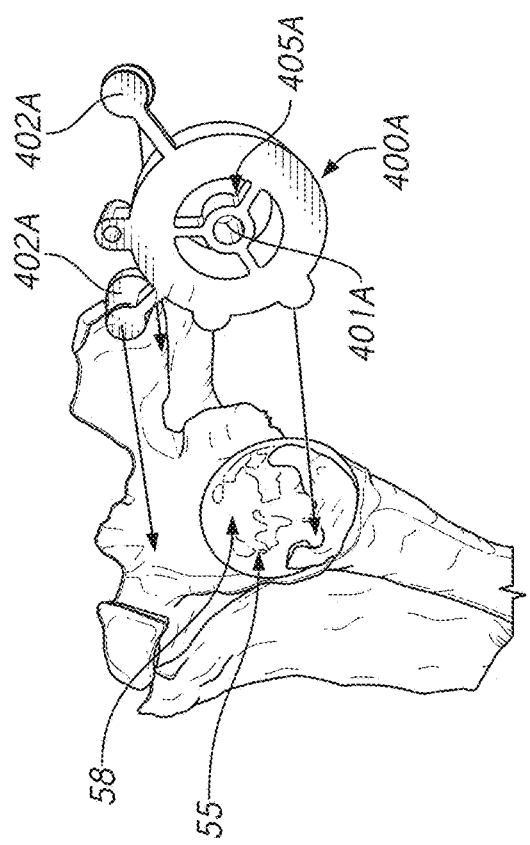
Figure 5C:
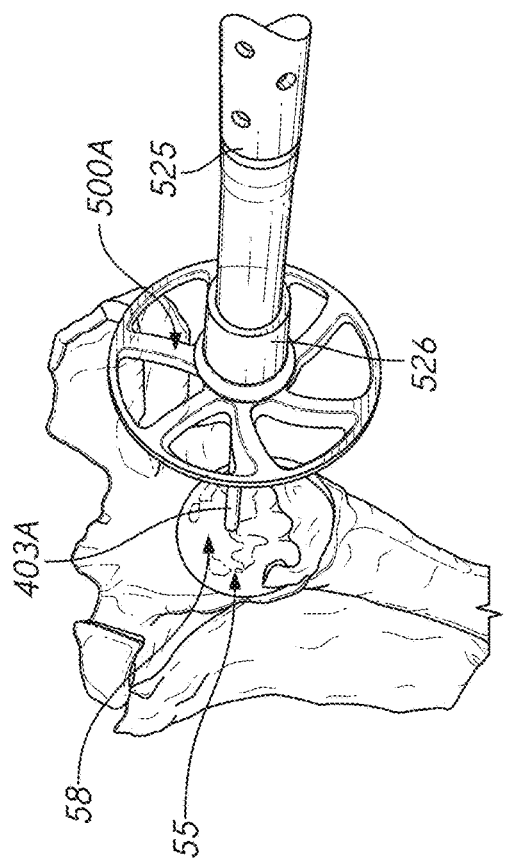
Figure 5E:
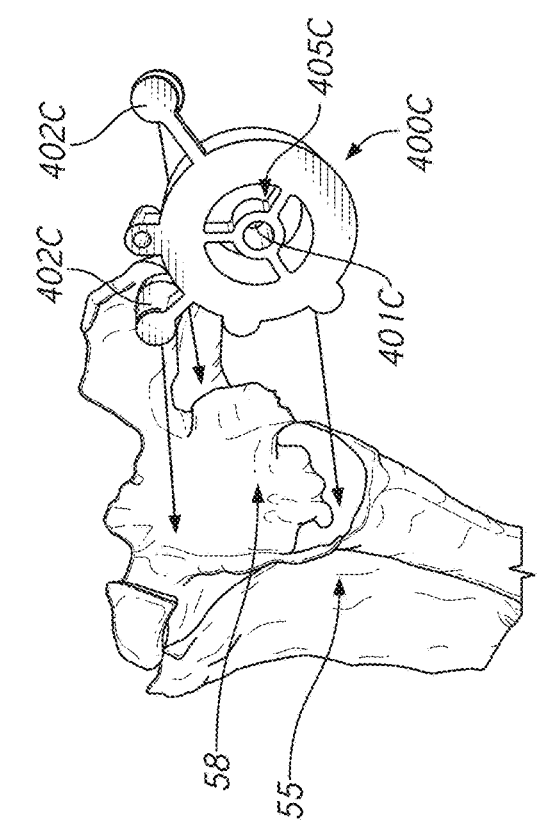
FIGS. 5E-5H illustrate an example method of reaming a portion of a scapula, according to another embodiment.

FIGS. 5B-5D illustrate an example method of reaming a portion of a scapula 55, according to various embodiments. Unless otherwise noted, the components of FIGS. 5B-5D may be the same as or generally similar to like-numbered components and features of FIGS. 1-5A, with reference numerals being appended by the letter "A." In the embodiment of FIGS. 5B-5D, the clinician can ream the glenoid 58 without using a reaming guide. Rather, the clinician can use image data of the patient's glenoid 58 and/or a model of the patient's glenoid 58 to selectively and accurately ream the glenoid 58 to form a reamed portion 75A, for example, to remove osteophytes and/or asymmetrical bone structure. Omitting the separate reaming guide can reduce the number of components in the kit and accordingly reduce costs.

In FIG. 5B, the clinician can use a guide pin guide 400A, which may be generally similar to or the same as guide pin guide 400, to ensure accurate placement of a guide pin 403A (see FIG. 5C). As explained above, the guide pin guide 400A can have a bone-facing surface that is patient-matched to the patient's specific, native bone structure, for example, based on image data. The guide pin guide 400A can accordingly be placed so as to conform to the contours of the patient's native scapula 55. As above, feet 402A extending from the central portion 405A can be placed against the glenoid 58, and the guide pin 403A can be inserted into the first opening 401A and into the bone.

Turning to FIG. 5C, the clinician can utilize a reaming device 500A connected to a reamer shaft 525 by way of a tip connector 526. The reaming device 500A can comprise any suitable reaming device, e.g., a standard full reamer, a partial reamer, etc. Instead of using a reaming guide to accurately define a reaming depth, patient-specific image data can be used to select a tip connector 526 that serves to define the depth of the reaming. Examples of the reaming device 500A and tip connector 526 may be similar to those set forth in FIG. 5I below. For example, as explained below, the tip connector 526 may comprise a protrusion 527C that, when pressed against the glenoid 58, defines the depth by which the glenoid 58 is to be reamed, based on the patient-specific image data. For example, based on the image data, the clinician can select a protrusion 527C having a length that, when pressed against the glenoid 58, ensures that the glenoid 58 is reamed to the appropriate depth and at the desired location on the glenoid 58. In some embodiments, the treatment kit can comprise a plurality of tip connectors 526 having different length protrusions 527C, and the clinician can select the appropriate tip connector 526 with a protrusion 527C having a length that provides the appropriate reaming depth based on the patient image data. In other embodiments, the treatment kit can comprise a patient-specific tip connector 526 (e.g., a single tip connector 526) that is manufactured to have a predetermined protrusion length based on patient-specific anatomy. The reaming device 500A can be guided over the guide pin 403A. With the selected tip connector 526 serving as a depth stop, the clinician can activate the reaming device 500A to at least partially ream the glenoid 58. The reaming device 500A can comprise any suitable type of reamer, e.g., a full reamer or a partial (e.g., pie-shaped) reamer. In some embodiments, the reaming device 500A may not be patient-specific. In other embodiments, the reaming device 500A can have a cutting surface or cutting member that is patient-specific, e.g., that is shaped to conform to the patient's anatomy.

In FIG. 5D, the reaming device 500A can be removed to expose the reamed portion 75A of the glenoid 58. As explained herein, the glenoid assembly 60A can be inserted into the glenoid 58. The glenoid assembly 60A may be the same as or generally similar to the glenoid assembly 60 described herein. For example, the anchor peg 64A and one or multiple screws 65A can anchor the glenoid assembly 60 to the glenoid 58 as explained further herein. Beneficially, the use of the selected tip connector 526 based on patient-specific image data can be used to accurately form the reamed portion 75A without requiring a separate reaming guide.

Figure 5G:
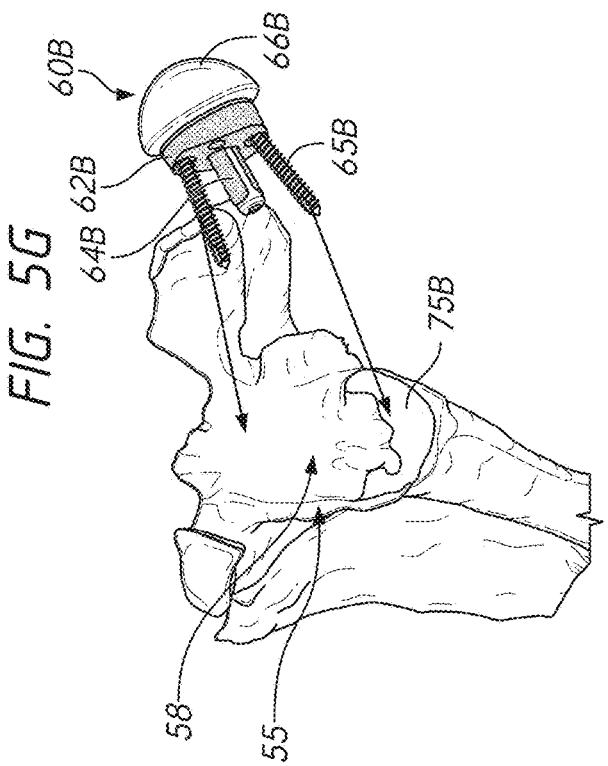
Figure 5F:
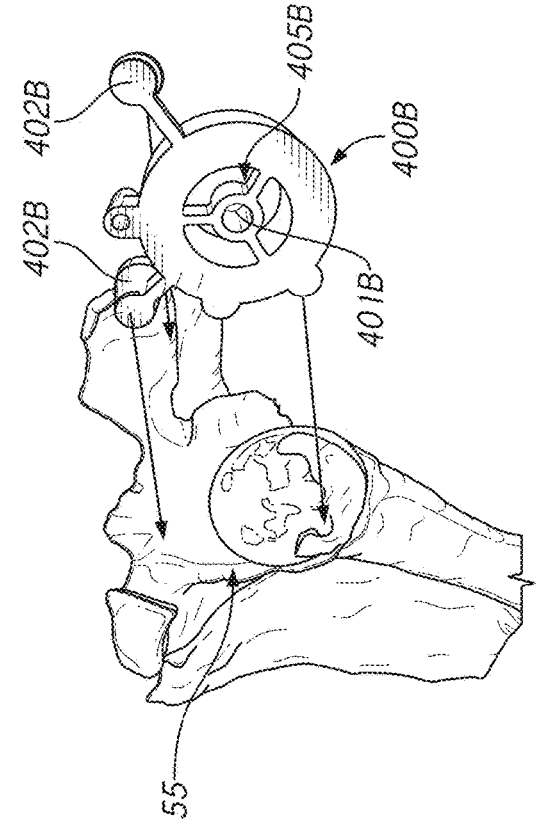
Figure 5H:
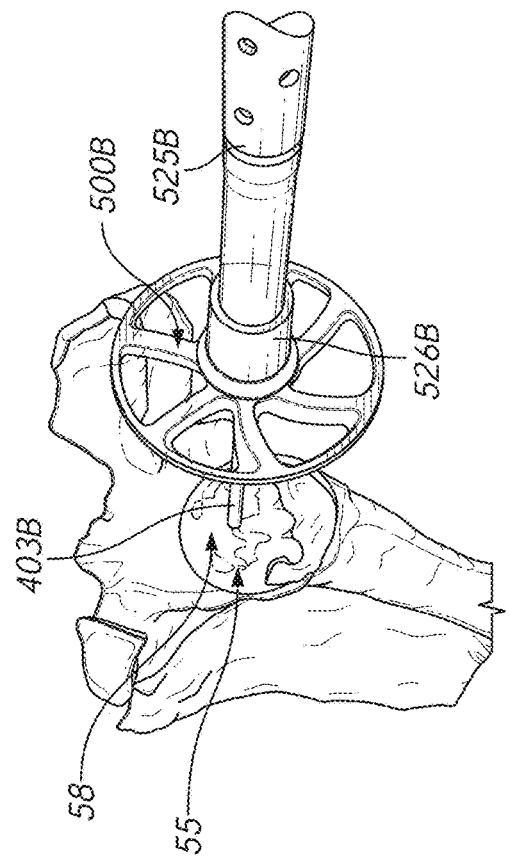
Figure 51:
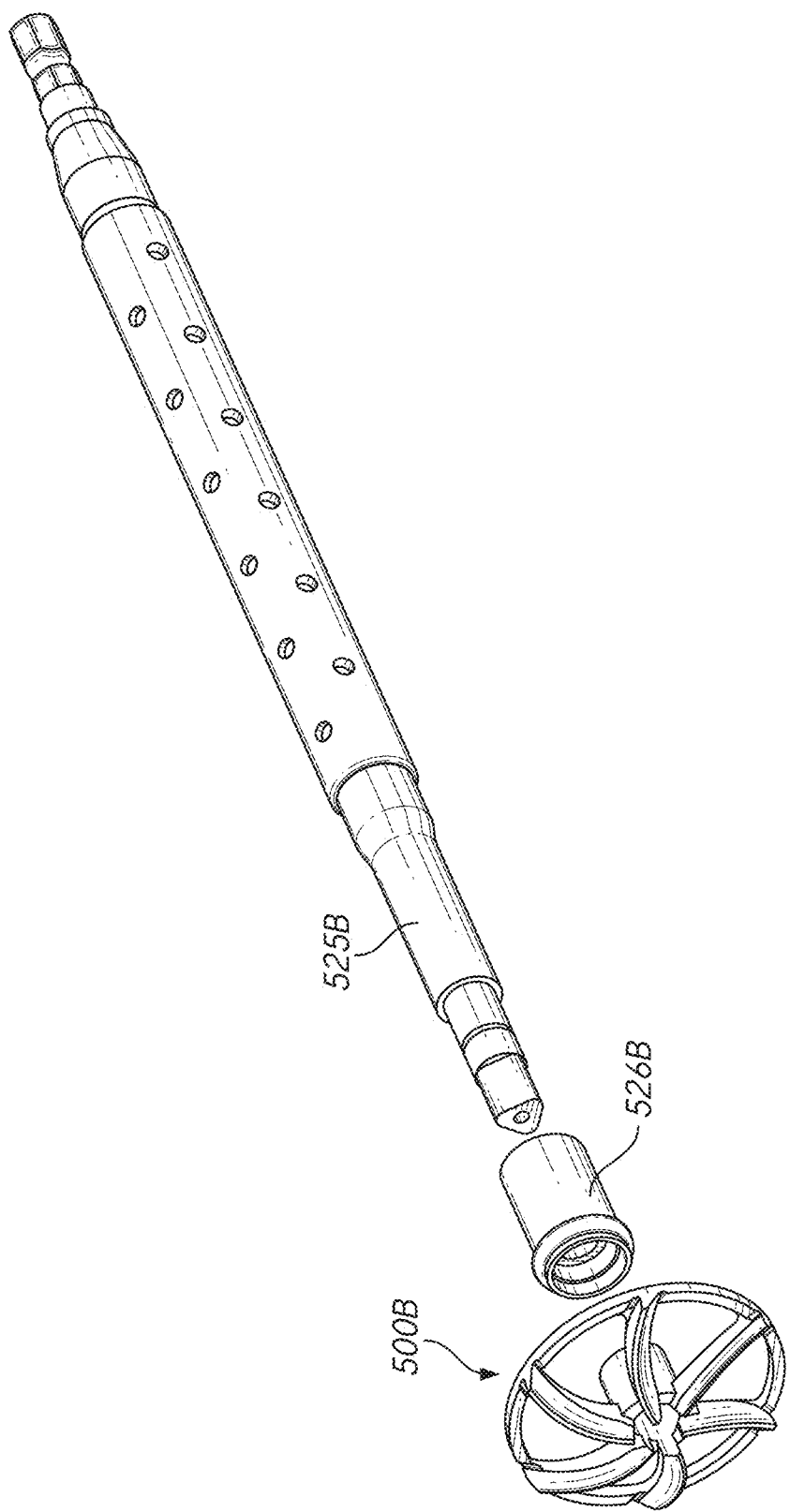

FIGS. 5E-5H illustrate an example method of reaming a portion of a scapula 55, according to another embodiment. Unless otherwise noted, the steps and components of FIGS. 5E-5H may be the same as or generally similar to like-numbered components of FIGS. 5B-5D, with reference numerals annotated with the letter "B." For example, as with the method of FIGS. 5B-5D, the guide pin guide 500B can be used to accurately place the guide pin 403B in FIG. 5E. The guide pin guide 500B of FIG. 5E can be patient-matched to the patient's native bone structure as explained above. In FIG. 5F, as with FIG. 5C, the tip connector 526B can be selected based on patient-specific image data in order to ream to the desired depth.

Turning to FIG. 5G, in some embodiments, the clinician may want to confirm that the reaming operation has accurately reamed the patient's bone structure, so that the glenoid assembly 60B is accurately positioned. In FIG. 5G, the treatment kit can include a second patient-matched guide pin guide 400C that includes a bone-facing surface that matches to the partially-reamed glenoid 58. For example, the surface of the second guide pin guide 400C can include a patient-matched partial reamed surface that matches the reamed portion 75B of the glenoid 58. If the clinician is satisfied that the patient-matched second guide pin guide 400C accurately matches the reamed portion 75B and the patient's native bone structure, then the clinician can proceed to FIG. 5H and install the glenoid assembly 60B. If the reaming is unsatisfactory, the clinician can continue or modify the reaming until the reamed portion 75B matches the patient-specific guide pin guide 400C.

FIGS. 5I-5K illustrate example reaming instruments, according to various embodiments. The instrument of FIG. 5I can be the same as or generally similar to the instrument shown in FIG. 5F. For example, FIG. 5I illustrates a reamer shaft 525B, a reaming device 500B, and a tip connector 526B that connects the reaming device 500B to the reamer shaft 525B. The tip connector 526B can be selected to provide a desired clearance between the reaming device 500B and the glenoid 58 based on, e.g., patient-specific image data.

FIG. 5J is a schematic side sectional view of a reamer shaft 525C, a reaming device 500C, and a tip connector 526C that connects the reaming device 500C to the reamer shaft 525C. The reamer shaft 525C, reaming device 500C, and tip connector 526C can be urged over the guide pin 403C. In the embodiment of FIG. 5J, the tip connector 526C can include a projection 527C that extends distal the reaming device 500C, e.g., distal a distal-most surface of the reaming device 500C. As explained herein, in some embodiments, the reaming device 500C can comprise a patient-specific reaming surface. In other embodiments, the reaming device 500C may not be patient-specific. During reaming, the clinician can urge the projection 527C of the tip connector 526C over the guide pin such that the distal end of the projection 527C contacts the glenoid 58. The projection 527C can accordingly serve to elevate the reaming device 500C above the glenoid 58 by a predetermined amount based on the patient-specific image data. Beneficially, unlike other reaming tips, the projection 527C of the tip connector 526C can serve to enhance lateral reaming, as opposed to medial reaming. For example, based on the patient-specific image data, the clinician can select a tip connector 526C based on a length of the projection 527C, e.g., based on how far beyond the reaming device 500C the projection 527C extends. As shown in FIG. 5J, the projection 527C can position the reaming device 500C above the glenoid 58 such that a first portion 58A (e.g., a lateral portion) of the glenoid 58 is reamed and a second portion 58B of the glenoid is spaced from the reaming device 500C and is not reamed.

In some embodiments, a treatment kit can include a plurality of tip connectors 526C having projections 527C at different lengths, e.g., at 0.5 mm increments in length. Based on the image data, the clinician can select a desired tip connector 526C which can provide lateral reaming at a predetermined depth. In other embodiments, a tip connector 526C can be manufactured to have a desired length of the projection 527C based on patient-specific data. The reaming device 500C and tip connector 526C can have an opening sized to receive the guide pin 403C. The reaming device 500C can be advanced over the guide pin 403C to at least partially ream the glenoid surface.

Turning to FIG. 5K, another reaming instrument is disclosed. Unless otherwise noted, the components of FIG. 5K may be similar to like-numbered components of FIG. 5J, with reference numerals appended by the letter "D." Unlike the embodiment of FIG. 5J, in FIG. 5K, the tip connector 526D can have a two-stage projection including a first projection 527D and a second projection 529D that has a diameter smaller than the diameter of the first projection 527D. In such embodiments, the clinician may not use a guide pin to ream the glenoid 58. Rather, the clinician can drill a pilot hole in the glenoid 58, and can insert the smaller-diameter second projection 529D of the tip connector 526D into the pilot hole. The pilot hole can serve as a depth stop such that the first projection 527D can rest upon the glenoid 58 when the second projection 529D extends into the pilot hole. Thus, in some embodiments, the clinician can select a tip connector 526D having lengths for the first and/or second projections 527D, 529D selected to provide a suitable amount of reaming based on patient specific data. As above, in some embodiments, the treatment kit can comprise a plurality of differently-sized connectors 526D. In other embodiments, the kit can comprise a patient-specific connector 526D manufactured based on patient-specific image data.

E. Patient Matched Anchor Peg Forming Guide

Figure 6:
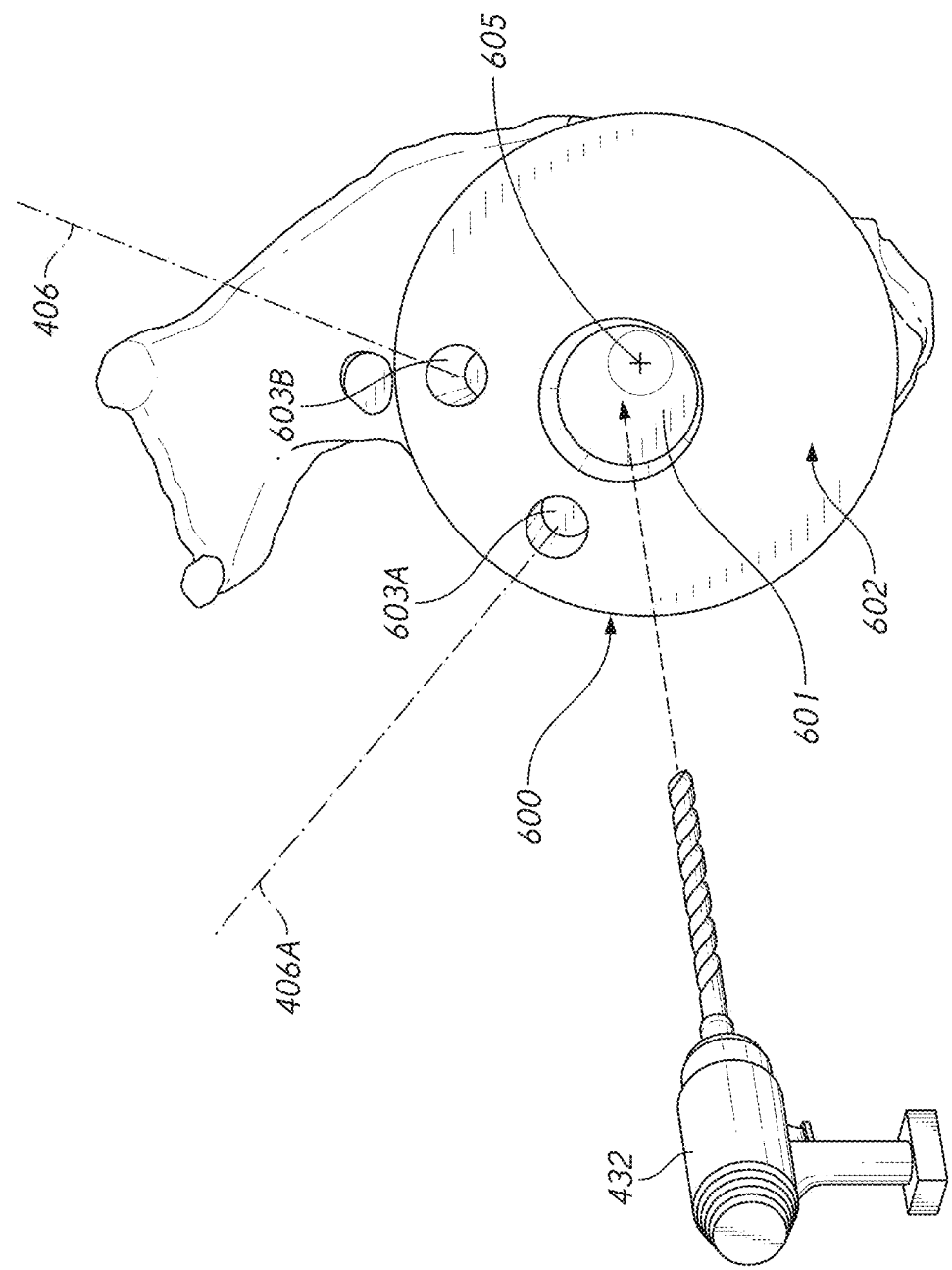
FIG. 6 is a schematic view of a glenoid during a method of preparation of the glenoid, in which an anchor peg preparation guide has been advanced onto the glenoid, the guide being secured to the glenoid and further illustrating an instrument being advanced through the guide to form a blind hole or other opening or channel into the glenoid to receive a baseplate anchor peg.
Figure 6B:
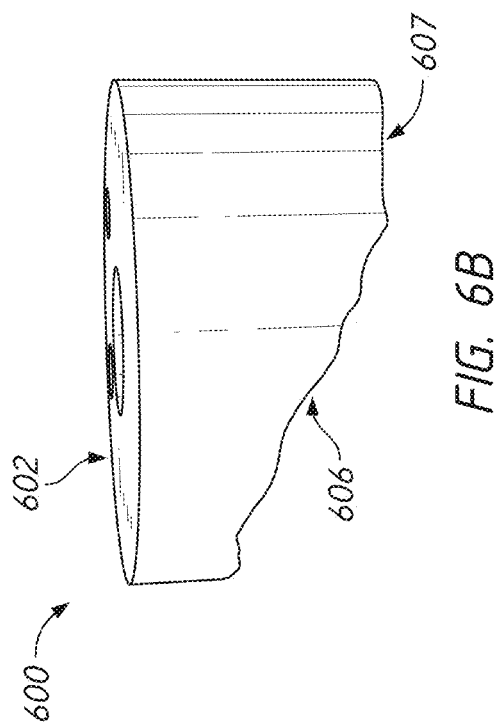
FIG. 6B is a side perspective view of the anchor peg channel forming guide illustrated in FIG. 6.
Figure 6A:
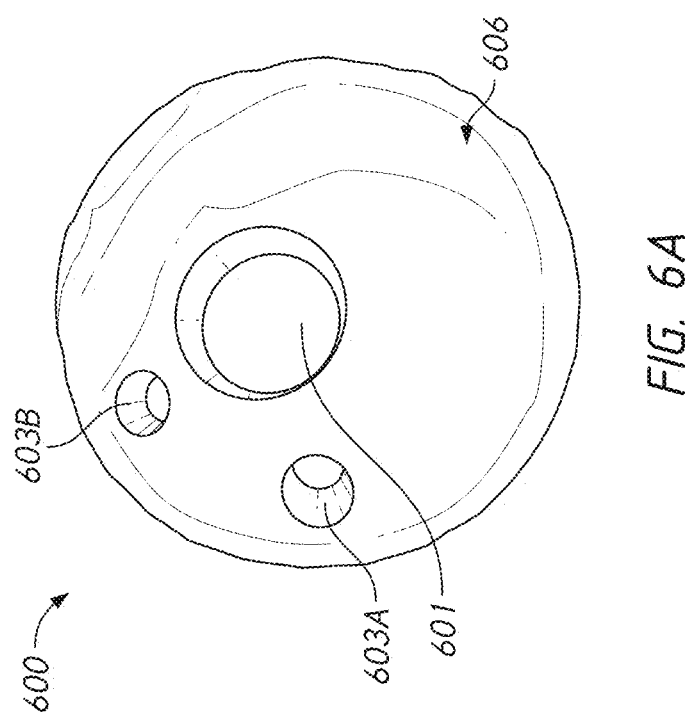
FIG. 6A is a medial side view of the anchor peg channel forming guide illustrated in FIG. 6.

FIGS. 6-6B illustrate an anchor peg channel forming guide 600 configured to help the clinician form an anchor peg channel 605 in the scapula of the patient. In some methods described herein, the anchor peg channel forming guide 600 is used in a method that can follow the steps illustrated in one or more of FIGS. 4 and 5. In other words, the guide 600 can be used to form an anchor peg channel in a partially reamed glenoid or in a glenoid that has not been reamed.

The anchor peg channel 605 can be positioned and sized to receive the anchor peg 64 of the glenoid baseplate 62. The anchor peg channel forming guide 600 can comprise a guide body having a patient-matched surface 606 shaped to conform to the scapula of the patient. A lateral surface 602 can be provided opposite the patient-matched surface 606. The lateral surface 602 can be generally planar in various embodiments. The anchor peg channel forming guide 600 can include a channel 601 disposed through the guide body of the guide 600. In various embodiments, the channel 601 can be positioned to be offset from the reaming axis R of the scapula. In various embodiments where no reaming is performed, the channel 601 can be positioned to be offset from a central portion such as may be defined by the first opening 401 of the guide 400.

A plurality of rotational alignment holes 603a, 603b can also be provide through the guide body of the guide 600. The rotational alignment holes 603a, 603b can be positioned to provide accurate rotational alignment of the anchor peg channel forming guide 600 relative to the scapula. The rotational alignment holes 603a, 603b can be used to secure the guide 600 such that is does not rotate in use or otherwise move. For example, pins 406a, 406a can be inserted through the rotational alignment holes 603a, 603b to align or to immobilize the guide 600 relative to the scapula. In some variations just one of the holes 603a, 603b is present if the guide 600 can be sufficiently stabilized or immobilized without a second of the holes 603a, 603b. As shown in FIG. 6, the clinician can use a drill 432 to drill through the channel 601 to form an anchor peg channel, which will have the same size as the inner periphery of the channel 601 and, in the case of an off-set peg baseplate (as in the case of the baseplate 162b), will be off-set from a hole or axis 605 in the scapula of the patient formed by the guide pin guide 400 through the first opening 401 thereof. In some embodiments, the drill 432 can be advanced over a guide pin (such as guide pin 403) formed through the guide 400 and can be centered on the reaming axis R. In such cases the guide 600 is optional. Once the anchor peg channel is formed in the glenoid through the channel 601, the guide 600 can be removed. As shown in FIGS. 6-6B, a center of a periphery of the guide body (in the illustrated embodiment aligned with the axis 605) can be spaced apart or offset from a center of the channel 601. The amount and direction of the offset can be patient specific. At least one peripheral hole (e.g., holes 603a or 603b) can be used to secure the guide body to the scapula.

Figure 7:
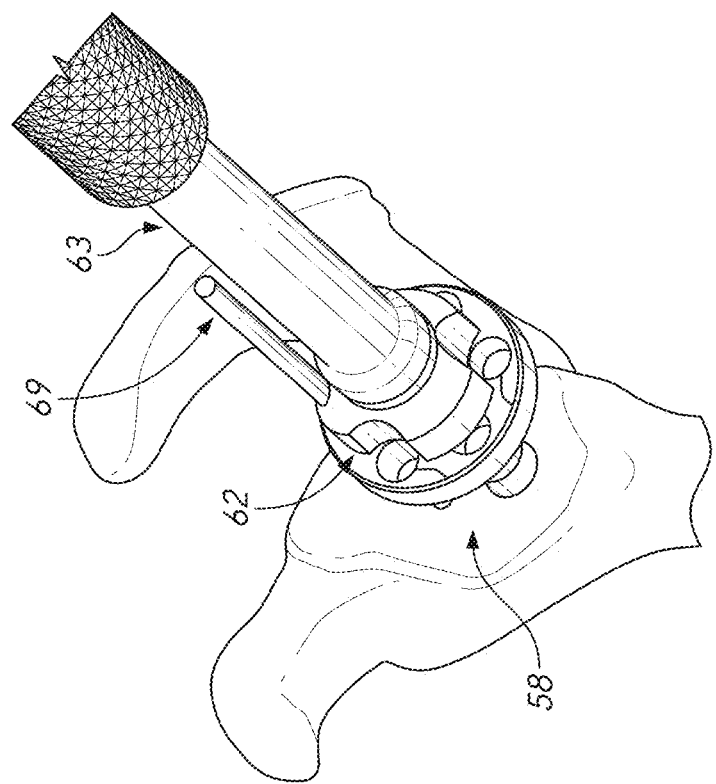
FIG. 7 is a schematic view of a glenoid during a method of implanting a glenoid baseplate into a glenoid.

In various embodiments, after the guide 600 has been used to form a channel in the scapula through the channel 601, the guide 600 can be removed from the scapula and an anchor peg 64 of a baseplate 62 (e.g., the peg 164B of the baseplate 162B) can be inserted into the anchor peg channel formed by the guide 600. As shown in FIG. 7, for example, a tool 63 can be used by the clinician to implant the anchor peg 162B into the anchor peg channel 605 formed in the glenoid 58. In other embodiments, the baseplate 162A can be inserted using the tool 63 if a centered peg channel is formed. A second guide pin 69 (which may the same as the guide pin 406 or 406a) can be inserted into the scapula and can provide for rotational alignment for the glenoid baseplate 62. For example, the second guide pin 69 may be inserted through the peripheral holes 404 of the guide 400 described above.

F. Screw Trajectory Guide

Figure 8:
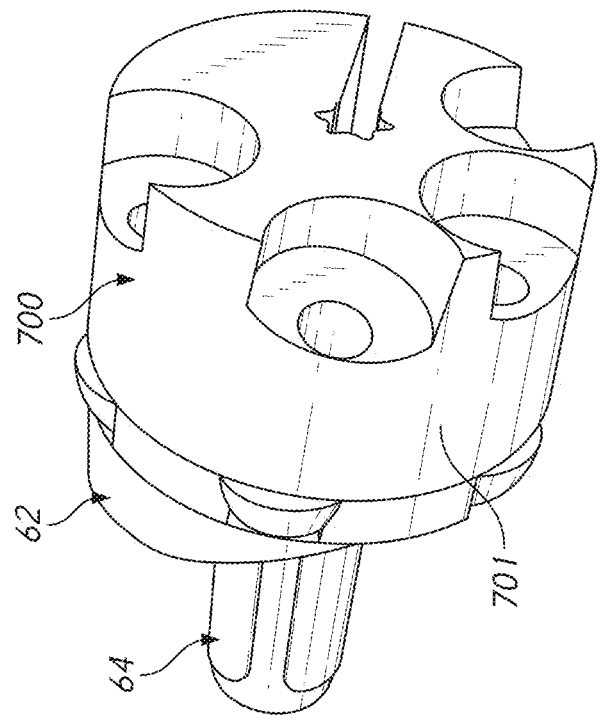
FIG. 8 is a perspective view of a peripheral screw trajectory guide mated to a glenoid baseplate, which can be used to prepare peripheral screw channels.

The glenoid baseplate 62 can be secured to the scapula with one or a plurality of screws. To ensure that the screws are aligned properly relative to the baseplate 62 and scapula, a screw trajectory guide 700 can be mated with the glenoid baseplate 62 to enable the clinician to insert the screws into the scapula of the patient. In some methods the screw trajectories or channels formed along such trajectories are made in a patient specific manner. The screw trajectory guide 700 can include a guide body 701 having a first surface 702a configured, e.g., shaped to mate with the glenoid baseplate 62 and a second surface 702b opposite the first surface 702b. A third surface 702c can be recessed from the second surface 702b and can be disposed between the first and third surfaces 702a, 702b. As shown in FIGS. 8-8D, the guide body 701 can include one or a plurality of protrusions 704 extending from the first surface 702a of the guide 700. The protrusions 704 can be sized and shaped to be inserted into corresponding apertures of the glenoid baseplate 62.

As shown in FIGS. 8A, 8B, and 8D, channels 705 can be disposed through the protrusions 704 and can extend from the third surface 702c through the protrusion 704 to a distal end 707 of the protrusion 704. The third surfaces 702c can serve as depth control surfaces and can be disposed at an elevation that is prescribed for the patient to control a depth of a peripheral screw hole formed in the scapula through the channels 705. As shown, axes labeled "Axe2" through "Axe5" can be defined through the channels 705. The axes Axe2 to Axe5 may be non-parallel to one another and selected to secure the baseplate to the scapula. A guide channel 703 can be formed through the guide body 701 so as to define axis Axe1 as shown in FIG. 8A. The guide channel 703 can be shaped and positioned to receive a guide wire or guide pin therethrough in one embodiment. The guide channel 703 can be provided over the guide pin to align the guide 700 with the baseplate 62. In some cases, the baseplate has a tapered proximal member (as shown in connection with baseplate 262 in FIG. 9) which can be received in the guide channel 703. The guide channel 703 can be internally tapered such that a secure connection can be provided between the guide and the baseplate 262. A slot 706 can extend from the guide channel 703 to an outer periphery of the guide body 701. The slot 706 can allow the guide 700 to flex to facilitate removal of the guide 700 from the proximal tapered member of the baseplate 262. The slot 706 can be optional if the connection between the guide 700 and the baseplate 262 does not involved mating tapered surface.

The clinician can drill holes in the patient's scapula through the peripheral channels 705 and through the corresponding apertures of the glenoid baseplate 62, the baseplate 262 or another baseplate disclosed herein. As explained above, the third surfaces 702c can be recessed to a depth to limit the depth of the corresponding peripheral screw holes. For example, the surfaces 702c can come into contact with a widened portion of a drill being advanced through the channels 705 stopping the drill from being inserted farther than intended.

Once the holes are drilled, the clinician remove the screw trajectory guide 700. Removing the guide 700 can include flexing the body of the guide about or opposite the slot 706. The clinician can secure the glenoid baseplate 62 to the glenoid 58 using one or a plurality of screws to be inserted through the apertures of the baseplate 62 and the screw holes formed in the scapula through the guide 700 and baseplate.

II. Kits and Systems for Glenoid Preparation and Baseplate Placement

The components described herein for preparation of the glenoid 58 and implantation of the glenoid baseplate 62 can be incorporated into a system 800 including a kit 800 of at least two of the components described herein. The kit 800 can include any two of the articles shown in FIG. 9 or combinations of these components with other components described herein in other kits.

Figure 9:
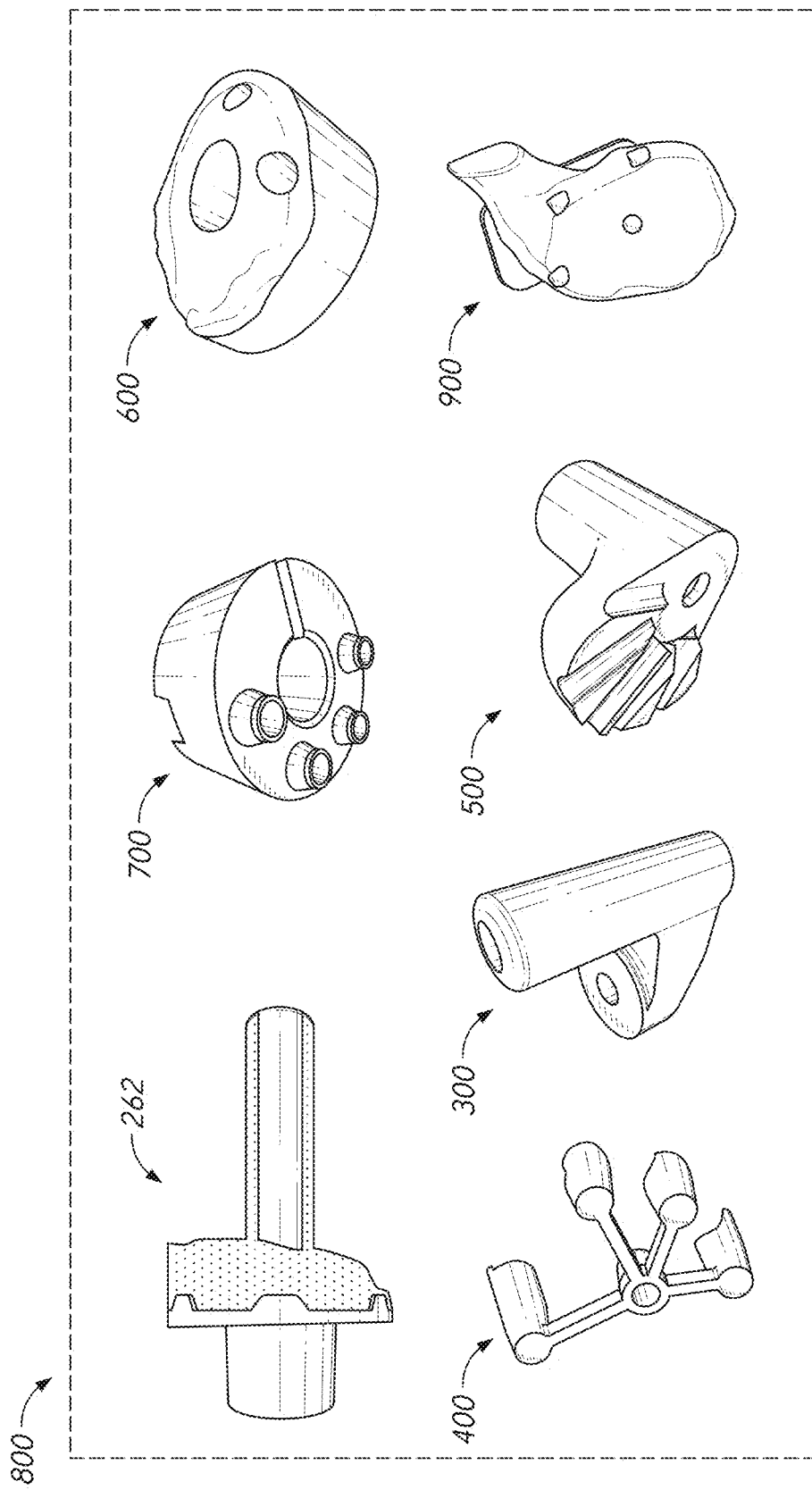
FIG. 9 illustrates one of several kits that can be provided including any two or more of the components shown therein or described herein.

For example, as shown in FIG. 9, the kit 800 can include at least two of, e.g., all of the glenoid baseplate 62 (such as any one or more of glenoid baseplates 162A, 162B, 262), the screw trajectory guide 700, the anchor peg forming guide 600, the guide pin guide 400, the partial reaming guide 300, and a three-dimensional (3D) model 900. The 3D model 900 of the patient's scapula can be based on the scan of the patient's anatomy to assist the clinician in preparing the shoulder for surgery. Beneficially, the collection of components in the kit 800 can enable the clinician to prepare and install the glenoid baseplate 62 with all of the components located in one tray or kit. Further, although not shown, the kit 800 can include any other suitable items, such as the reaming device 500 and other system components. The kit 800 can include the partial reaming guide 300 and the reaming device 500. The kit 800 can include the baseplate 162B and the anchor peg channel forming guide 600. The kit 800 can include the baseplate 162A and the other articles shown in FIG. 9 but can exclude the anchor peg channel forming guide 600. Any suitable number of components can be provided in the kit.

Terminology

As used herein, the relative terms "lateral" and "medial" shall be defined relative to the anatomy. Thus, medial refers to the direction toward the midline and lateral refers to the direction away from the midline.

Although certain embodiments and examples have been described herein, it will be understood by those skilled in the art that many aspects of the delivery systems shown and described in the present disclosure may be differently combined and/or modified to form still further embodiments or acceptable examples. All such modifications and variations are intended to be included herein within the scope of this disclosure. A wide variety of designs and approaches are possible. No feature, structure, or step disclosed herein is essential or indispensable.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Moreover, while illustrative embodiments have been described herein, the scope of any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to the examples described in the present specification or during the prosecution of the application, which examples are to be construed as non-exclusive. Further, the actions of the disclosed processes and methods may be modified in any manner, including by reordering actions and/or inserting additional actions and/or deleting actions. It is intended, therefore, that the specification and examples be considered as illustrative only, with a true scope and spirit being indicated by the claims and their full scope of equivalents.

Conditional language used herein, such as, among others, "can," "might," "may," "e.g.," and the like, unless specifically stated otherwise, or otherwise understood within the context as used, is generally intended to convey that some embodiments include, while other embodiments do not include, certain features, elements, and/or states. Thus, such conditional language is not generally intended to imply that features, elements, blocks, and/or states are in any way required for one or more embodiments or that one or more embodiments necessarily include logic for deciding, with or without author input or prompting, whether these features, elements and/or states are included or are to be performed in any particular embodiment.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±1%, ±5%, ±10%, ±15%, etc.). For example, "about 0.01 inches" includes "0.01 inches." Phrases preceded by a term such as "substantially" include the recited phrase and should be interpreted based on the circumstances (e.g., as much as reasonably possible under the circumstances). For example, "substantially linear" includes "linear."

What is claimed is:

1. A method for performing a shoulder surgery involving preparation of a glenoid surface of a patient's shoulder, comprising:
   guiding a guide pin into the glenoid surface along a reaming axis;
   placing a partial reaming guide in contact with the glenoid surface over the guide pin, wherein the partial reaming guide comprises:
      a guide body including a patient-matched surface shaped to conform to a portion of a scapula of a patient;
      a reamer depth stop surface at a first height above the patient-matched surface, the reamer depth stop surface positioned to serve as a depth stop for a reaming device to control a depth of reaming; and
      a first hole through the guide body extending from the reamer depth stop surface to the patient-matched surface, the first hole aligned with a reaming axis;
   advancing a reamer over the guide pin to ream the glenoid surface;
   further advancing the reamer over the guide pin until the reamer contacts the partial reaming guide, whereby such contact limits reaming to only a portion of the glenoid surface.

2. The method of claim 1, further comprising forming a channel in the scapula medially from the glenoid surface, the channel configured to receive an anchor peg of a glenoid baseplate.

3. The method of claim 2, further comprising advancing a drill over the guide pin to form an anchor peg channel centered on the reaming axis.

4. The method of claim 2, further comprising advancing an anchor peg channel forming guide toward the glenoid surface, the anchor peg channel forming guide comprising a body and an aperture formed inward of a periphery of the body and securing the anchor peg channel forming guide against the glenoid surface with the aperture off-set from the reaming axis.

5. The method of claim 1, wherein advancing the reamer and further advancing the reamer comprises reciprocating a reaming surface of the reamer about an angle of less than 180 degrees relative to the reamer axis.

6. The method of claim 1, further comprising inserting an anchor peg of a glenoid baseplate into an anchor peg channel formed in the glenoid surface.

7. The method of claim 6, further comprising coupling a screw trajectory guide with the baseplate and forming one or more screw holes in the scapula through the screw trajectory guide and the baseplate.

8. The method of claim 7, further comprising controlling a depth of the one or more screw holes with a corresponding depth control surface of the screw trajectory guide.

9. The method of claim 1, further comprising defining a reaming axis based on image data responsive to a scan of a scapula of a patient.

10. A method for performing shoulder surgery involving preparation of a glenoid surface of a patient's shoulder, comprising:
- guiding a guide pin into the glenoid surface along a reaming axis;
- placing a partial reaming guide in contact with the glenoid surface over the guide pin, wherein the partial reaming guide comprises:
  - a guide body including a patient-matched surface shaped to conform to a portion of a scapula of a patient;
  - a reamer depth stop surface at a first height above the patient-matched surface, the reamer depth stop surface positioned to serve as a depth stop for a reaming device to control a depth of reaming; and
  - a first hole through the guide body extending from the reamer depth stop surface to the patient-matched surface, the first hole aligned with a reaming axis;
- selecting a tip connector based on patient-specific image data;
- connecting a reaming device to a handle by way of the selected tip connector; and
- advancing the reaming device over the guide pin until the reaming device contacts the partial reaming guide, whereby such contact limits reaming to only a portion of the glenoid surface.

11. The method of claim 10, further comprising, after the advancing, placing a guide pin guide over the at least partially reamed glenoid surface to verify the at least partial reaming, the guide pin guide having a patient-matched bone-facing surface.

12. The method of claim 10, further comprising installing a glenoid assembly in the glenoid surface after the advancing.

13. The method of claim 10, wherein selecting the tip connector comprises selecting the tip connector from a plurality of differently-sized tip connectors.

14. The method of claim 10, wherein selecting the tip connector comprises forming the tip connector based on the patient-specific image data.

15. The method of claim 10, further comprising a plurality of tip connectors with distally-extending projections having different lengths.

* * * * *